(12) United States Patent
Dalbøge et al.

(10) Patent No.: US 6,190,905 B1
(45) Date of Patent: Feb. 20, 2001

(54) ENZYME WITH PROTEASE ACTIVITY

(76) Inventors: Henrik Dalbøge, Parkvej 28, Virum DK-2830 (DK); Stephan Christgau, Raveskovsvej 10A, DK-2820 Gentofte (DK); Lene Nonboe Andersen, Birkerød, Lindehøjvej 9 DK-3460 (DK); Lene Venke Kofod, Ugerløse, Brorfeldevej 8 DK-4350 (DK); Markus Sakari Kauppinen, Copenhagen N, Egegade 10, 5. DK-2200 (DK); Jack Bech Nielsen, Ole Olsens Allé, DK-2900 Hellerup (DK); Claus Dambmann, Søborg, Høje Gladsaxe 61, 7. th. DK-2860 Søborg (DK)

( * ) Notice: Under 35 U.S.C. 154(b), the term of this patent shall be extended for 0 days.

(21) Appl. No.: 09/408,257

(22) Filed: Sep. 29, 1999

Related U.S. Application Data

(63) Continuation of application No. 09/190,982, filed on Nov. 12, 1998, now Pat. No. 5,998,190, which is a continuation of application No. 08/578,551, filed on Feb. 1, 1996, now Pat. No. 5,854,050, which is a continuation of application No. PCT/DK94/00274, filed on Jul. 5, 1994.

(30) Foreign Application Priority Data

Jul. 6, 1993 (DK) .................................................. 0811/93

(51) Int. Cl.$^7$ ...................................................... D06M 16/00
(52) U.S. Cl. ............................................. 435/264; 435/219
(58) Field of Search ..................................... 435/264, 219, 435/212, 223, 224, 225

(56) References Cited

U.S. PATENT DOCUMENTS

| | | | |
|---|---|---|---|
| 3,492,204 | 1/1970 | Koaze et al. | 195/66 |
| 3,509,024 | 4/1970 | Jorgens et al. | 195/66 |

OTHER PUBLICATIONS

Takahashi et al., J. of Biological Chem., vol. 266, No. 29, pp. 19480–19483 (1991).
Berka et al., Gene, vol. 125, pp. 195–198 (1993).

*Primary Examiner*—Nashaat T. Nashed
(74) *Attorney, Agent, or Firm*—Steve T. Zelson; Cheryl H. Agris

(57) ABSTRACT

An isolated and purified enzyme exhibiting protease activity at a pH of 4–7 which exhibits protease in 5% hydrogen peroxide and which is encoded by a DNA sequence which hybridizes to a DNA sequence depicted in SEQ ID NO: 1 or 2. Methods are described for using the protease compositions in reducing vescosity, cleaning contact lenses, baking, and preparing animal feed.

4 Claims, 8 Drawing Sheets

ENZYME WITH PROTEASE ACTIVITY

CROSS-REFERENCE TO RELATED APPLICATIONS

Figure 1:
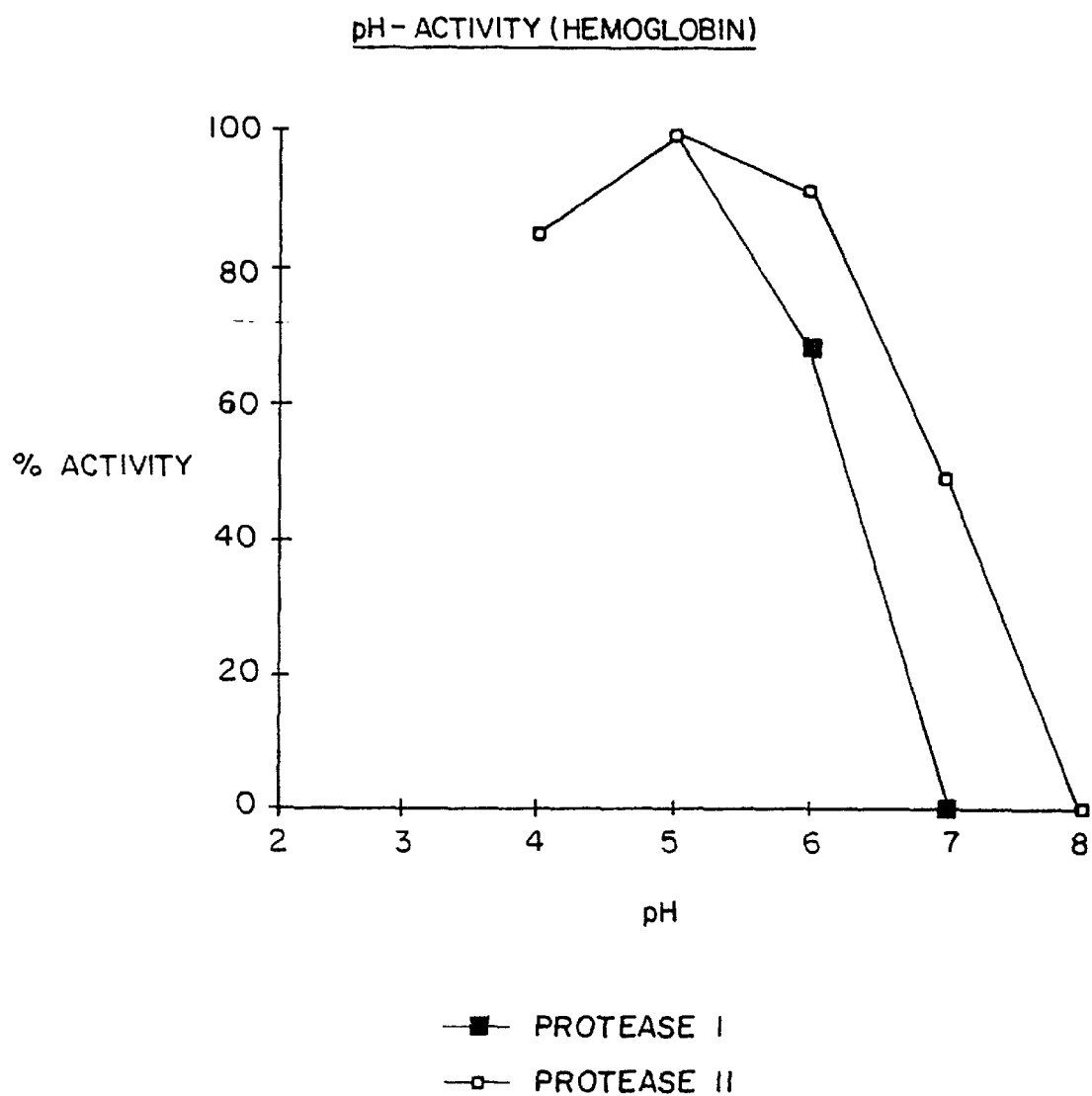

This application is a continuation of application Ser. No. 09/190,982, filed Nov. 12, 1998, now U.S. Pat. No. 5,998,190, which is a continuation of No. 08/578,551 filed on Feb. 1, 1996, now U.S. Pat. No. 5,854,050, which is a continuation of application Ser. No. PCT/DK94/00274 filed on Jul. 5, 1994, and claims priority under 35 U.S.C. 119 of Danish application serial no. 0811/93 filed on Jul. 6, 1993, the contents of which are fully incorporated herein by reference.

FIELD OF INVENTION

The present invention relates to a DNA construct encoding an enzyme with protease activity, a method of producing the enzyme, an enzyme with protease activity, and an enzyme preparation containing the enzyme.

BACKGROUND OF THE INVENTION

Proteases are enzymes capable of cleaving peptide bonds. Acid proteases (i.e. proteases having an acidic pH optimum) have been found to be produced by a number of different organism including mammals and microbes. For instance, microbial acid proteases have been found to be produced by bacterial strains such as strains of Bacillus sp. (JP 01240184), fungal strains, e.g. of Rizopus sp. (EP 72978), Schytalidium sp. (JP 48091273), Sulpholobus sp. and Thermoplasma sp. (WO90 10072) and Aspergillus sp. (JP 50121486, EP 82 395).

JP 3058794 discloses the cloning of a gene encoding an acid protease from *R. niveus* and the recombinant expression thereof. The cloning and expression of a gene from *Cryphonectira parasitica* encoding an aspartic protease is described by Choi et al. (1993). Takahashi et al. (1991), Inoue et al. (1991), and JP 407 5586 discloses the cloning of a gene from *Aspergillus niger* encoding an acid proteinase (Protease A).

Berka et al. (1990) disclose a gene encoding the aspartic proteinase aspergillopepsin A from *Aspergillus awamori*. The cloning of a gene encoding the aspartic proteinase aspergillopepsin O from *Aspergillus oryzae* is described by Berka et al. (1993). The cloning of a gene encoding the acid protease (PEPA) from *Aspergillus oryzae* is disclosed by Gomi et al. (1993).

Acid proteases are widely used industrially, e.g. in the preparation of food and feed, in the leather industry (e.g. to dehair hides), in the production of protein hydrolysates and in the wine making and brewing industry.

There is a need for single-component acid proteases for many different applications, especially in the food and feed industry.

SUMMARY OF THE INVENTION

It is an object of the present invention to prepare a single-component protease.

Accordingly, in a first aspect the invention relates to a DNA construct comprising a DNA sequence encoding an enzyme exhibiting protease activity, which DNA sequence comprises the DNA sequence shown in SEQ ID No. 1 or an analogous sequence thereof being at least 80% homologous to the DNA sequence shown in SEQ ID No. 1.

In a second aspect the invention relates to a DNA construct comprising a DNA sequence encoding an enzyme exhibiting protease activity, which DNA sequence comprises the DNA sequence shown in SEQ ID No. 2 or an analogous sequence thereof being at least 80% homologous to the DNA sequence shown in SEQ ID No. 2.

The DNA sequence shown in SEQ ID No. 1 encodes an enzyme which in the following disclosure is referred to as Protease I. The enzyme encoded by the DNA sequence shown in SEQ ID No. 2 is referred to as Protease II.

By a data base homology search it has been found that the DNA sequence shown in SE ID Nos. 1 and 2 are generally novel. The highest homology of the DNA sequence shown in SEQ ID No. 1 to known protease genes was found to be 74.7% to the *Aspergillus niger* acidic proteinase A as determined for an overlap of 538 nucleotides. The highest homology to protease II was found to be 75.5% to the *Aspergillus oryzae* aspergillopepsin O as determined for an overlap of 343 nucleotides.

In further aspects the invention relates to an expression vector harbouring a DNA construct of the invention, a cell comprising the DNA construct or expression vector and a method of producing an enzyme exhibiting protease activity which method comprises culturing said cell under conditions permitting the production of the enzyme, and recovering the enzyme from the culture.

In a still further aspect the invention relates to an enzyme exhibiting protease activity, which enzyme is encoded by a DNA construct of the invention as defined above or produced by the method of the invention.

In a further important aspect the invention relates to an enzyme with protease activity, which is active at a pH below 7.0 and in the presence of up to 3% hydrogen peroxide. In the present context, the term "is active" as used about the enzyme is intended to indicate that the enzyme is capable of hydrolysing a substrate under the above-mentioned conditions, e.g. as described in example 5 herein.

This enzyme of the invention which is active at a pH below 7.0 and in the presence of up to 3% hydrogen peroxidase and which removes more than 80% of the lysozyme from the lenses under the conditions specified in example 5 is termed the "$H_2O_2$-stable protease" in the following disclosure. This enzyme is believed to be generally novel.

Also, the present invention provides an enzyme with protease activity, which enzyme is active at a pH below 7.0 and which is specific towards Phe-Val or Lys-Tyr linkages. The term "specific" is intended to indicate that the enzyme, when the substrate is bovine glucagon, primarily cleaves these linkages.

Protease I and protease II described herein are preferred examples of an enzyme of the invention. The enzymes have been found to be acid proteases, i.e. proteases which has an acid pH optimum.

By the present invention it is possible to provide the protease in a highly purified form, i.e. greater than 75% pure, and more preferably greater than 90% pure as determined by SDS gel electrophoresis as described in the Materials and Methods section herein.

In final aspects the invention relates to an enzyme preparation comprising an enzyme of the invention and the use of the enzyme or enzyme preparation for various purposes in which modification or degradation of protein-containing substances is desirable.

DETAILED DESCRIPTION OF THE INVENTION

The DNA construct, vector and method of the invention

In the present context the term "analogue" used to define the DNA construct of the invention is understood to include any DNA sequence which encodes an enzyme with protease activity and which is at least 80% homologous to the DNA sequence shown in SEQ ID No. 1 or 2, respectively. The analogous DNA sequence may be a DNA sequence which hybridizes to the same probe as the DNA coding for the protease enzyme under the following conditions: presoaking in 5×SSC and prehybridizing for 1 h at –55° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at ~55° C. followed by washing three times in 2×SSC, 0.2% SDS at 55° C. for 30 minutes. The analogous DNA sequence is preferably at least 90% homologous to the sequence shown in SEQ ID No. 1 or 2, preferably at least 95% homologous to said sequence.

The analogous DNA sequence may, e.g., be isolated from another organism or may be one prepared on the basis of the DNA sequence shown in SEQ ID No. 1 or 2, such as by introduction of nucleotide substitutions which do not give rise to another amino acid sequence of the protease but which correspond to the codon usage of the host organism into which the DNA construct is introduced or nucleotide substitutions which do give rise to a different amino acid sequence and therefore, possibly, a different protein structure which might give rise to a protease mutant with different properties than the native enzyme. Other examples of possible modifications are insertion of one or more nucleotides into the sequence, addition of one or more nucleotides at either end of the sequence, or deletion of one or more nucleotides at either end or within the sequence.

Furthermore, it is preferred that the protease encoded by the analogous DNA sequence is immunologically cross-reactive with an antibody raised against a purified protease encoded by the DNA sequence shown in SEQ ID No. 1 or 2.

The nucleotide probe with which the analogue of the DNA sequence shown in SEQ ID No. 1 can hybridize may, e.g. be prepared on the basis of any of the following DNA sequences or any combination thereof:

```
(a) AATTAAGCAT CCTCCATCTT                                          (SEQ ID NO:3)
(b) CAAAGCTCAA TCTCGCTAAC                                          (SEQ ID NO:4)
(c) TCCCGCTCTT CTCTCGATCT                                          (SEQ ID NO:5)
(d) CATCATCCCA ATAACTCGGA                                          (SEQ ID NO:6)
(e) CAAAATGAAG ACCTCTGCTC                                          (SEQ ID NO:7)
(f) TCTTGACCGC TGGCCTGTTG                                          (SEQ ID NO:8)
(g) GCACCGCTGC TATTGCTGCT                                          (SEQ ID NO:9)
(h) CCTCTCACCG CGAAGCGCGC                                          (SEQ ID NO:10)
(i) ACGTGCTCGC GCTGCCAAGC                                          (SEQ ID NO:11)
(j) TGGCACCAGC CGCAAGAGCA                                          (SEQ ID NO:12)
(k) AGGGGGGTCT CAAGCCCGGC                                          (SEQ ID NO:13)
(l) ACCCAGCGAG GCCATAACCT                                          (SEQ ID NO:14)
(m) GACCGGCTCC AAGAACACCG                                          (SEQ ID NO:15)
(n) GAGGTACTCG TCCAACTGGG                                          (SEQ ID NO:16)
(o) CCGGCGCCGT GCCAT                                               (SEQ ID NO:17)
(p) AATTAAGCAT CCTCCATCTT CAAAGCTCAA TCTCGCTAAC TCCCGCTCTT         (SEQ ID NO:18)
    CTCTCGATCT CATCATCCCA ATAACTCGGA CAAAATGAAG ACCTCTGCTC
    TCTTGACCGC TGGCCTGTTG GCACCGCTGC TATTGCTGCT CCTCTCACCG
    CGAAGCGCGC ACGTGCTCGC GCTGCCAAGC TGGCACCAGC CGCAAGAGCA
    AGGGGGGTCT CAAGCCCGGC ACCCAGCGAG GCCATAACCT GACCGGCTCC
    AAGAACACCG GAGGTACTCG TCCAACTGGG CCGGCGCCGT GCCAT
```

These sequences constitute partial sequences of the DNA sequence shown in SEQ ID No. 1 or analogues of such sequences.

The nucleotide probe with which the analogue of the DNA sequence shown in SEQ ID No. 2 can hybridize may, e.g., be prepared on the basis of any of the following DNA sequences or any combination thereof:

```
(p1) CTGCTTCTCC TTCTCTTCCT                                         (SEQ ID NO:19)
(q)  CCTCGTGATA TCTGCTTGAA                                         (SEQ ID NO:20)
(r)  CATCTCCTCA TCATGGTCGT                                         (SEQ ID NO:21)
(s)  CCTCAACAAG GTGCAGCCTT                                         (SEQ ID NO:22)
(t)  CTTCTGGGTC TGACCACCGC                                         (SEQ ID NO:23)
(u)  CGCCACTGGT CCCCTGGCCG                                         (SEQ ID NO:24)
(v)  AGCCGCAGGC TTCTGTCCGG                                         (SEQ ID NO:25)
(w)  TCAAGAACTT CTCCGTCAAG                                         (SEQ ID NO:26)
(x)  CAGGTCGAGA AGGCGGGCAG                                         (SEQ ID NO:27)
(y)  CAAGGGACGT ACCGTTAACC                                         (SEQ ID NO:28)
```

```
                                    -continued
(z)   TGCCGGGTCT GTATGCGAAT                                              (SEQ ID NO:29)
(aa)  GCGCTGGCCA AGTATGGCGC                                              (SEQ ID NO:30)
(bb)  CCAGGTGCGG CCAGCGTCAA                                              (SEQ ID NO:31)
(cc)  GGCCGCCGCC GTCAGTGGCA                                              (SEQ ID NO:32)
(dd)  GCGTCGTGAC CACCCGCAGG CCAACGACG                                    (SEQ ID NO:33)
(ee)  CTGCTTCTCC TTCTCTTCCT CCTCGTGATA TCTGCTTGAA CATCTCCTCA
      TCATGGTCGT CCTCAACAAG GTGCAGCCTT CTTCTGGGTC TGACCACCGC
      CGCCACTGGT CCCCTGGCCG AGCCGCAGGC TTCTGTCCGG TCAAGAACTT
      CTCCGTCAAG CAGGTCGAGA AGGCGGGCAG CAAGGGACGT ACCGTTAACC
      TGCCGGGTCT GTATGCGAAT GCGCTGGCCA AGTATGGCGC CCAGGTGCGG
      CCAGCGTCAA GGCCGCCGCC GTCAGTGGCA GCGTCGTGAC CACCCGCAGG  CCAACGACG   (SEQ ID NO:34)
```

These sequences constitute partial sequences of the DNA sequence shown in SEQ ID No. 2 or analogues of such sequences.

A DNA sequence of the invention may be isolated by a general method involving cloning, in suitable vectors, a DNA library from *Aspergillus aculeatus*, transforming suitable yeast host cells with said vectors, culturing the host cells under suitable conditions to express any enzyme of interest encoded by a clone in the DNA library, and screening for positive clones by determining any protease activity of the enzyme produced by such clones.

A more detailed description of this screening method is given in Example 1 below and in WO 93/11249, the contents of which is hereby incorporated by reference.

The DNA sequence coding for the enzyme may for instance be isolated by screening a cDNA library of *Aspergillus aculeatus*, e.g. strain CBS 101.43, publicly available from the Centraalbureau voor Schimmelcultures, Delft, NL, and selecting for clones expressing the appropriate enzyme activity (i.e. protease activity as defined by the ability of the enzyme to hydrolyse peptide bonds in proteins and peptides). The appropriate DNA sequence may then be isolated from the clone by standard procedures, e.g. as described in Example 1.

It is expected that a DNA sequence coding for a homologous enzyme, i.e. an analogous DNA sequence, may be derived by similarly screening a cDNA library of another microorganism, in particular a fungus, such as a strain of another Aspergillus sp., in particular a strain of *A. aculeatus* or *A. niger*, a strain of a Trichoderma sp., in particular a strain of *T. harzianum*, or *T. reesie*, a strain of a Fusarium sp., in particular a strain of *F. oxysporum*, a strain of Rhizopus sp., e.g. *R. niveus*, a strain of Schytalidum sp., or a strain of a Humicola sp.

Alternatively, the DNA sequence of the invention may, in accordance with well-known procedures, conveniently be isolated from DNA from an appropriate organism by use of synthetic oligonucleotide probes prepared on the basis of a DNA sequence disclosed herein. For instance, a suitable oligonucleotide probes may be prepared on the basis of any of the partial nucleotide sequences shown above.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the protease should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the protease, the promoter and the terminator, respectively, and to insert them into suitable vectors are well known to persons skilled in the art (cf., for instance, Sambrook et al., *Molecular Cloning. A Laboratory Manual,* Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of *Aspergillus oryzae* as a host microorganism is described in EP 238 023 (of Novo Noridisk A/S), the contents of which are hereby incorporated by reference. The host cell may also be a yeast cell, e.g. a strain of Saccharomyces, in particular *Saccharomyces cerevisiae, Saccharomyces kluyveri* or *Saccharomyces uvarum,* a strain of Schizosaccaromyces sp., such as *Schizosaccharomyces pombe,* a strain of Hansenula sp., Pichia sp., Yarrowia sp. such as *Yarrowia lipolytica,* or Kluyveromyces sp. such as *Kluyveromyces lactis.*

In a still further aspect, the present invention relates to a method of producing an enzyme with protease activity, wherein a suitable host cell transformed with a DNA construct of the invention encoding the enzyme is cultured under conditions permitting the production of the enzyme, and the resulting enzyme is recovered from the culture.

The medium used to culture the transformed host cells may be any conventional medium suitable for growing the host cells in question. The expressed protease may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The enzyme of the invention

Preferably, the protease of the invention (e.g. The $H_2O_2$-stable or the Lys-Tyr or Phe-Val specific protease) is active at a pH in the range of 2–7, such as at a pH below 6.0, e.g. in the range of 2–6, and most preferably in the pH range of 4–6.

It will be understood that both acidic proteases are active in the presence of 0.01–5% hydrogen peroxide, such as 0.1–5%, 05.–4%, 1–4% of 2–3% hydrogen peroxide and are applicable to contact lens cleaning.

A preferred example of an $H_2O_2$-stable protease of the invention is the enzyme encoded by the DNA sequence shown in SEQ ID No. 1 or an analogue thereof as defined above, which is at least 80% homologous to said DNA sequence.

A preferred example of the Lys-Tyr or Phe-Val specific protease of the invention is the enzyme encoded by the DNA sequence shown in SEQ ID No. 2 or an analogue thereof as defined above, which is at least 80% homologous to said DNA sequence.

The enzyme of the invention is preferably immunologically reactive with an antibody raised against a purified protease derived from *Aspergillus aculeatus*, CBS 101.43 and being encoding by the DNA sequence shown in SEQ ID No. 1 or 2. In the present context, the term "derived from" is intended not only to indicate a protease produced by strain CBS 101.43, but also a protease encoded by a DNA sequence isolated from strain CBS 101.43 and produced in a host organism transformed with said DNA sequence.

While the $H_2O_2$-stable protease and the Lys-Tyr or Phe-Val specific protease of the invention both were obtained from a strain of the fungal species *Aspergillus aculeatus*, it is contemplated that such enzymes are obtainable from other organisms as well, in particularly microorganisms.

Thus, the enzyme of the invention is preferably obtainable from a bacterium or a fungus such as a strain of Aspergillus, Rhizopus, Trichoderma, e.g. *T. reesei* or *T. harzianum*, Penicillium, Fusarium, Schytalidium or Humicola, e.g. *H. insolens* or *H. lanuginosa*, or a strain of Bacillus.

Examples of Aspergillus sp. include *A. niger*, *A. oryzae* or *A. aculeatus*, such as *A. aculeatus* CBS 101.43.

In a still further aspect, the present invention relates to an enzyme preparation useful for the degradation or modification of protease containing materials, said preparation being enriched in an enzyme exhibiting protease activity as described above.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Gamanase, Celluclast or Celluzyme or protease and/or exopeptidase-containing enzyme preparations such as Neutrase®, Alcalase® or Flavourzyme® (all available from Novo Nordisk A/S). In the present context, the term "enriched" is intended to indicate that the protease activity of the enzyme preparation has been increased, e.g. with an enrichment factor of at least 1.1, conveniently due to addition of an enzyme of the invention prepared by the method described above.

Alternatively, the enzyme preparation enriched in an enzyme exhibiting protease activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation according to the invention may be used as an agent for degradation or modification of plant cell walls. Some proteins, like extensins, are components of plant cell walls. Proteases will therefore facilitate the degradation or modification of plant cell walls. Such a protease containing plant cell wall degrading enzyme preparation can be used for many different applications like extraction of oil from plant sources like olives and rape or for production of juice from different fruits like apples, pears and citrus.

The enzyme preparation may additionally contain one or more other plant cell wall degrading enzymes such as a pectin lyase, pectate lyase, endoglucanase, arabinanase, xylanase, glucanase, galactanase, mannanase, α-galactosidase, rhamnogalacturonase, pectin acetylesterase, polygalacturonase, protease, exo-peptidase or pectin methylesterase. The preparation may further contain one or more enzymes exhibiting exo-activity on the same substrates as the above-mentioned endo-enzymes. The proteases according to the invention work at the same pH and temperature conditions as many other cell wall degrading enzymes, and are thereby particular well suited for such applications.

The additional enzyme(s) may be producible by means of a microorganism belonging to the genus Aspergillus, preferably *Aspergillus niger*, *Aspergillus aculeatus*, *Aspergillus awamori* or *Aspergillus oryzae*, or Trichoderma.

The protease enzyme preparation according to the invention may also be used in the wine industry, to prevent haze or to dissolve haze, as proteins often take part in the undesirable haze formation. The proteases according to the invention are active under the conditions present under fermentation and maturation of wine, and they are therefore particular useful for this application.

The enzyme or enzyme preparation of the invention may be used in baking, e.g. in order to weaken the gluten components of flour so as to obtain a softening of so-called hard four. The use of weak flour is important for the preparation of dough which must be very extensible and not elastic, e.g. in the preparation of extruded baked products, biscuits and other products which must keep their original shape during transport and baking. The proteases of the invention constitute a desirable alternative to conventionally used agents for weakening of flour, such as sodium metabisulphite (SMS). The use of SMS is considered to be undesirable because of potential health risks.

The protease preparation may also be used in the food and feed industry to improve the digestibility of proteins. For instance, the enzyme or enzyme preparation may be added to animal feed or may be used to process animal feed, in particular feed for piglets or poultry. Thereby, the digestibility of components of the feed may be increased resulting in an improved growth rate and efficiency of feed utilisation of the animals, cf. Brenes et al. (1993).

Further the enzyme or enzyme preparation of the invention may be useful to make protein hydrolysates from, e.g., vegetable proteins like soy, pea, lupin or rape seed protein, milk like casein, meat proteins, or fish proteins. The protease may be used for protein hydrolysates to improve the solubility, consistency, taste, or fermentability, to reduce antigenicity or for other purposes to make food, feed or dedical products. The protease may be used alone or together with other proteases or together with other enzymes like exopeptidases. The use of the protease of the invention together with exopeptidase rich enzyme preparations will improve the taste of the protein hydrolysates.

The protease preparation may also be used to modify proteins, like reducing viscosity caused or partially caused by proteins. Such viscosity problems are known in the processing of different protein containing plant materials like soya and peas.

Furthermore, the enzyme or enzyme preparation may be used in the processing of fish or meat, e.g. to change texture and/or viscosity.

The protease preparation may also be used to facilitate fermentative processes, like yeast fermentation of barley, malt and other raw materials for the production of e.g. beer.

Furthermore, the enzyme or enzyme preparation of the invention may be useful in the leather industry e.g. to remove hairs from hides. The low pH optimum of the protease is an advantage as the subsequent tanning of the hides is carried under acid conditions. The protease preparation is useful for production of peptides from proteins, where it is advantages to use a cloned enzyme essentially free from other proteolytic activities.

Further the protease preparation can be used to degrade protein in order to facilitate purification of or to upgrade different products, like in purification or upgrading of gums, like guar gum, xanthan gum, degumming of silk, or improvement of the quality of wool.

Due to the stability towards hydrogen peroxide both proteases of the invention are of particular use for cleaning of contact lenses and other applications involving the use of hydrogen peroxide, in which protein-containing material is to be removed.

For the above uses, the dosage of the enzyme preparation of the invention and other conditions under which the preparation is used may be determined on the basis of methods known in the art.

The invention is further described in the accompanying drawing in which

Figure 2:
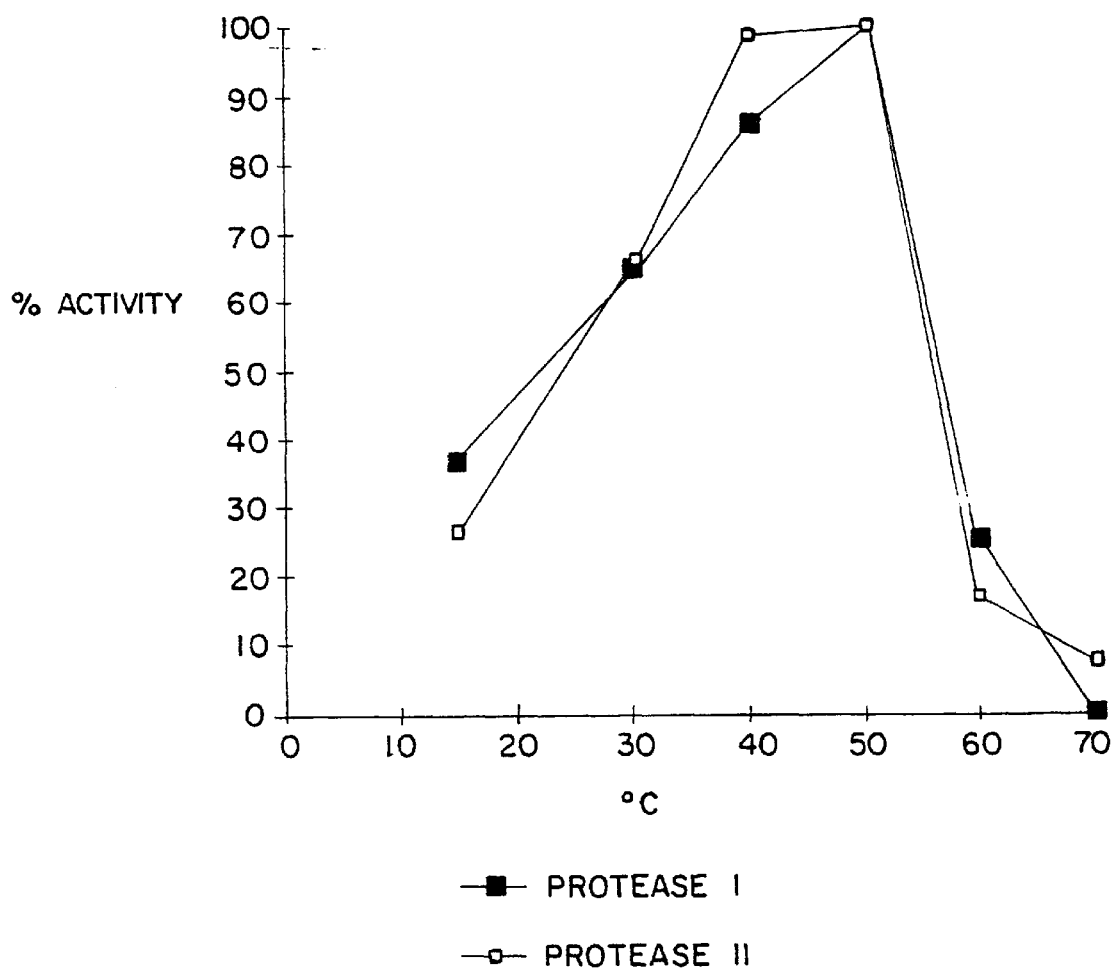
Figure 3:
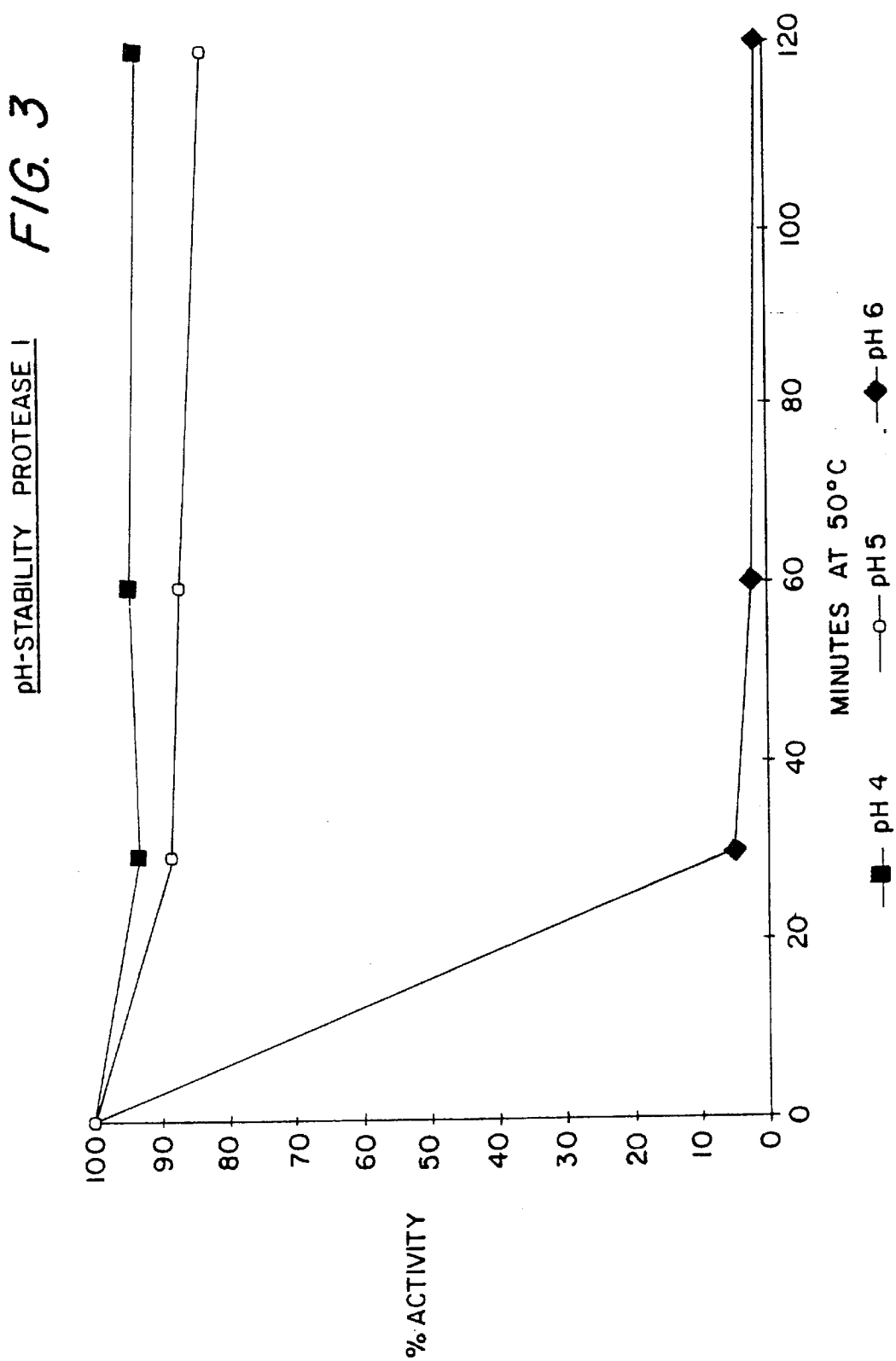
Figure 4:
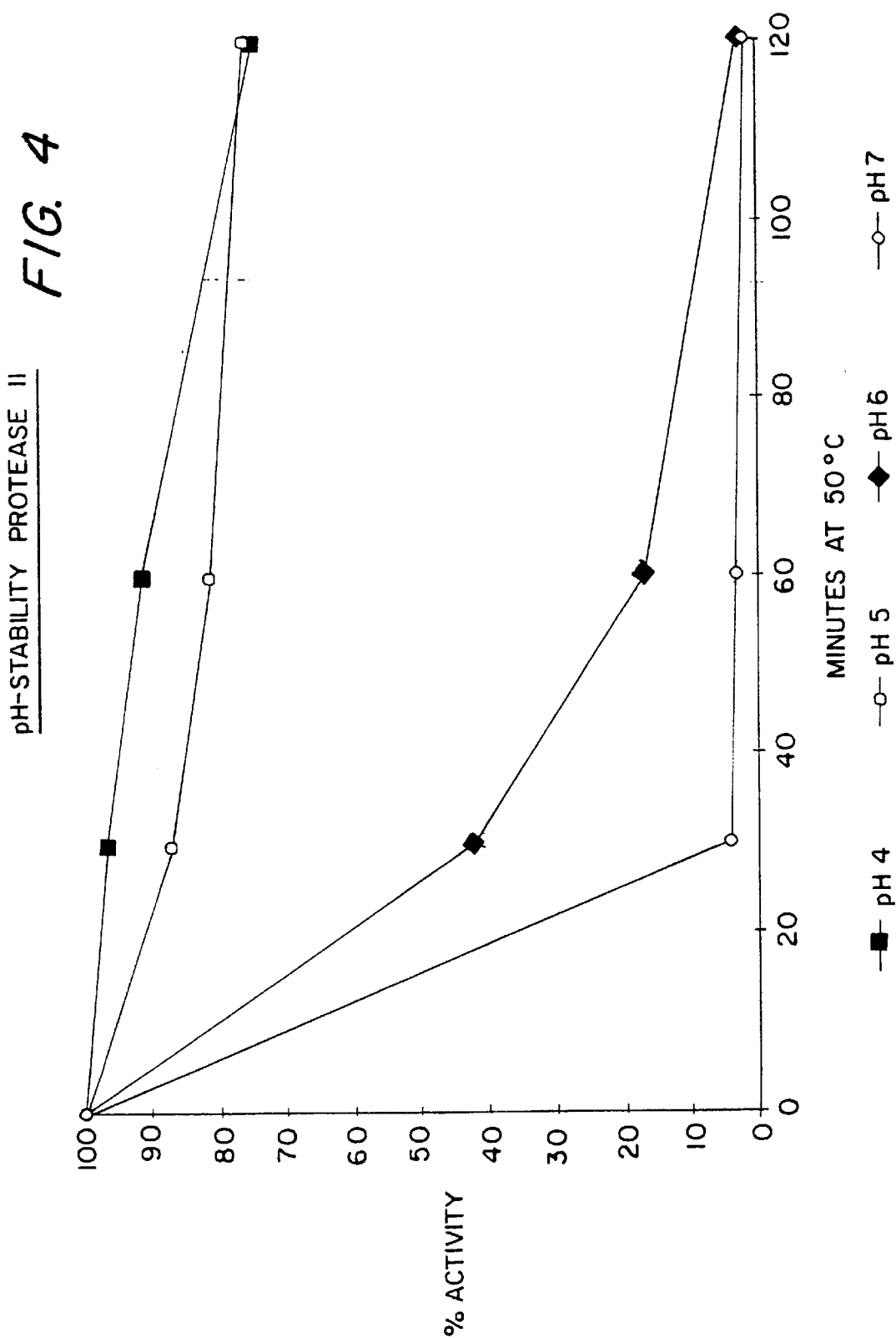
Figure 5:
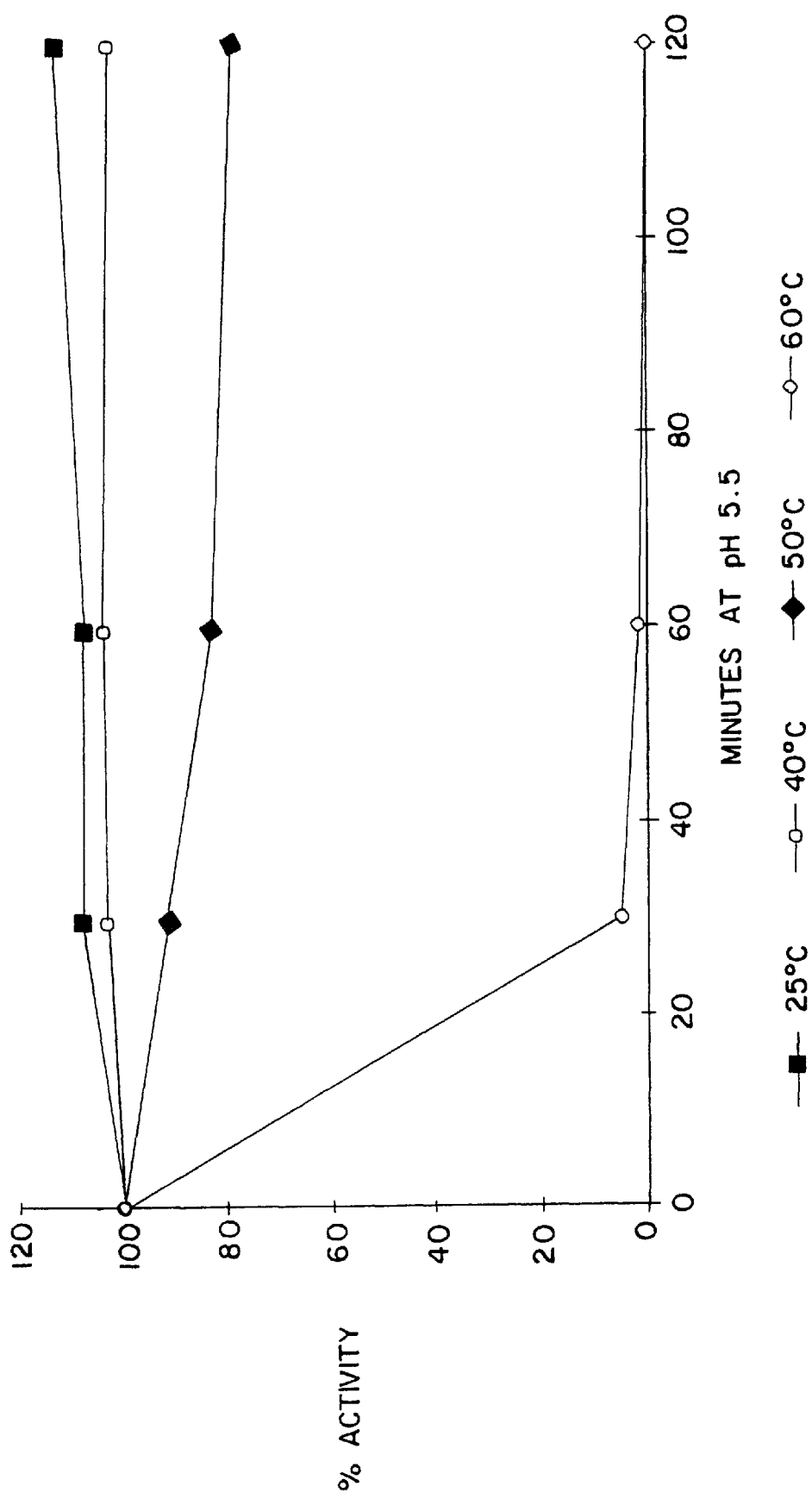
Figure 6:
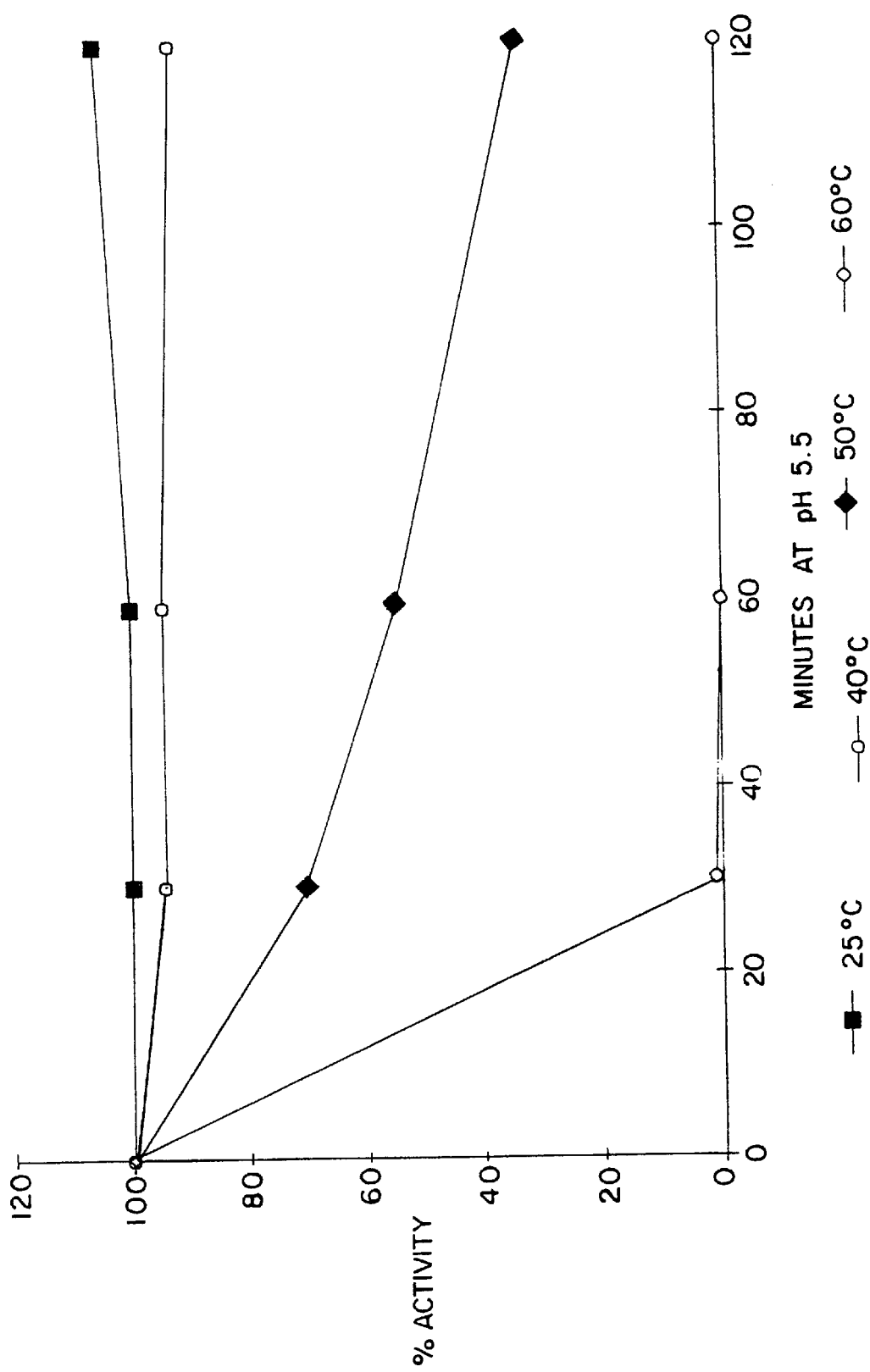
Figure 7:
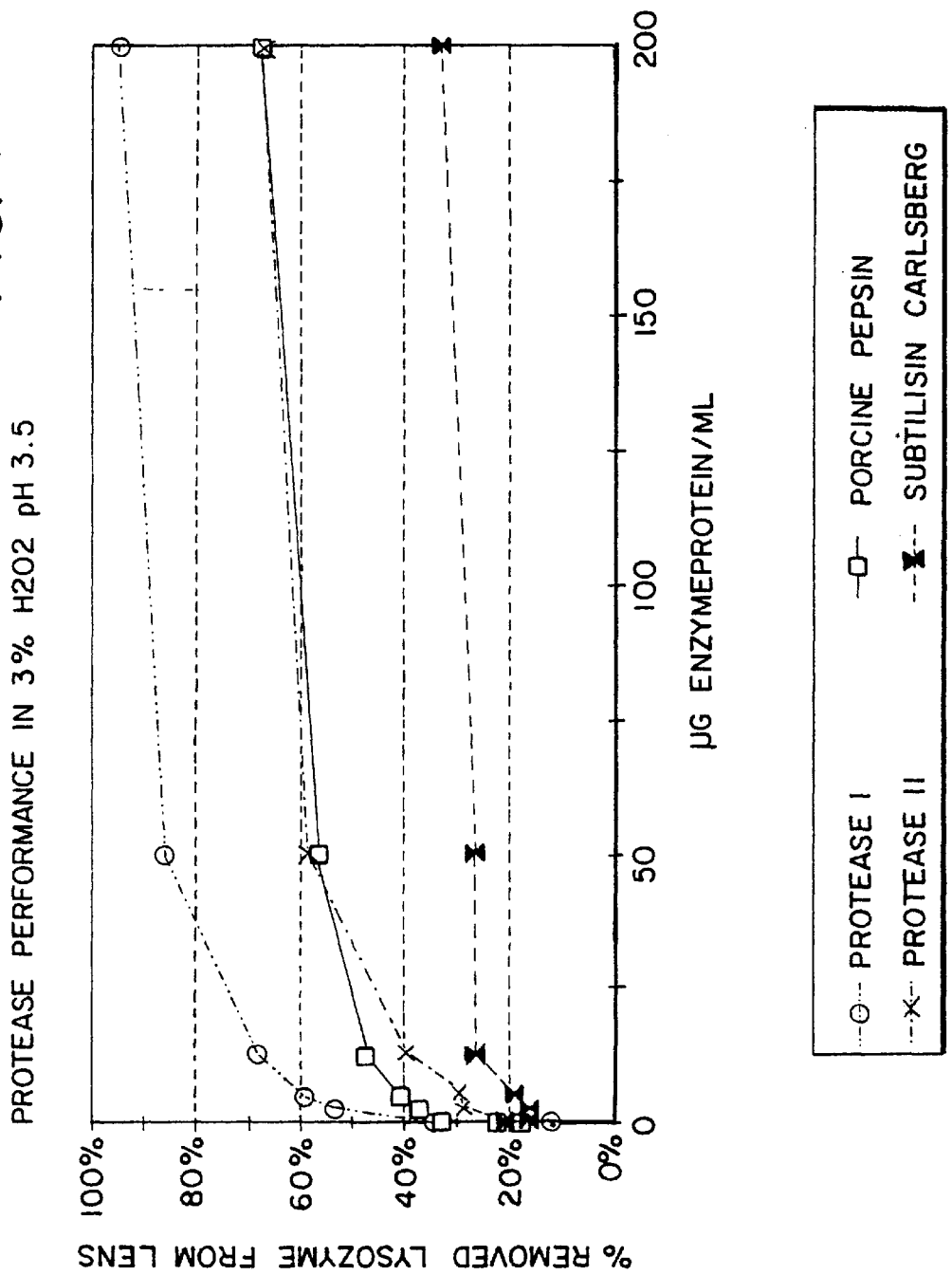
Figure 8:
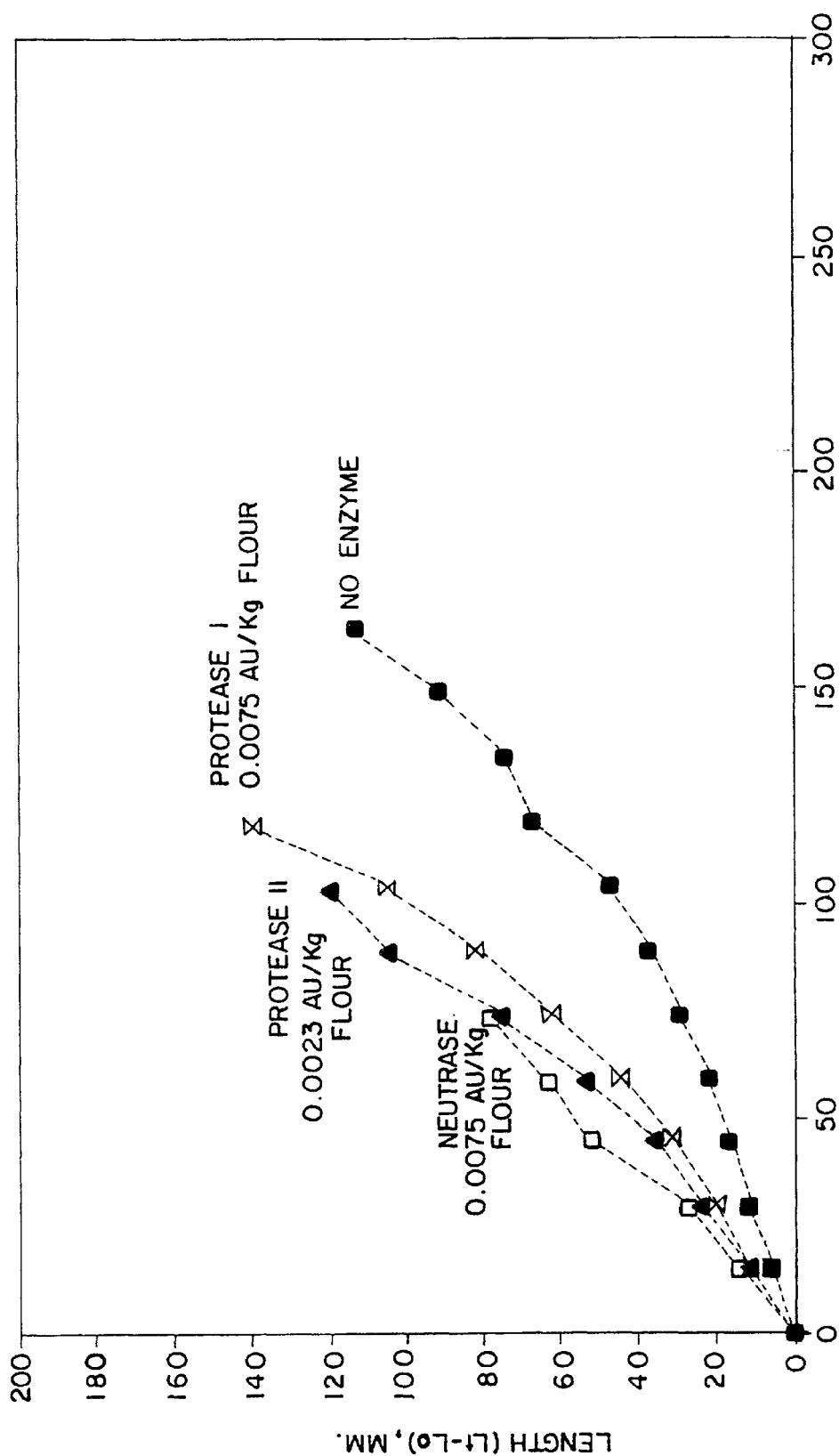

FIG. 1 the pH activity profiles of Protease I and II, respectively,

FIG. 2 the temperature-activity profiles of Protease I and II, respectively,

FIGS. 3 and 4 the pH stability of Protease I and II, respectively,

FIGS. 5 and 6 the temperature stability of Protease I and II, respectively,

FIG. 7 the performance of various proteases in the cleaning of contact lenses, and FIG. 8 the gluten stretching effect of an enzyme of the invention.

The invention is described in further detail in the following examples which are not in any way intended to limit the scope of the invention as claimed.

MATERIALS AND METHODS

Donor Organism mRNA was isolated from *Aspergillus aculeatus*, CBS 101.43, grown in a soy-containing fermentation medium with agitation to ensure sufficient aeration. Mycelia were harvested after 3–5 days' growth, immediately frozen in liquid nitrogen and stored at −80° C.

Yeast Strains

The *Saccharomyces cerevisiae* strain used was yNG231 (MAT alpha, leu2, ura3-52, his 4-539, pep4-delta 1, cir+) or JG169 (MATα; ura 3-52; leu 2-3, 112; his 3-D200; pep 4-113; prc1::HIS3; prb1:: LEU2; cir+).

Plasmids

The expression plasmid pYHD17 containing the yeast TPI promoter was prepared from the commercially available plasmid pYES II (Invitrogen). The plasmid and the construction thereof is further described in WO 93/11249, the contents of which is hereby incorporated by reference.

The Aspergillus expression vector pHD414 is a derivative of the plasmid p775 (described in EP 238 023). The construction of pHD414 is further described in WO 93/11249. pHD414 contains the *A. niger* glucoamylase terminator and the *A. oryzae* TAKA amylase promoter.

Extraction of Total RNA

The total RNA was prepared by extraction with guanidinium thiocyanate followed by ultracentrifugation through a 5.7 M CsCl cushion essentially as described by Chirgwin et al., 1979 and in WO 93/11249.

Isolation of poly(A)$^+$RNA

The poly(A)$^+$RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1×column loading buffer (20 mM Tris-Cl, pH 7.6, 0.5 M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1 M NaCl, 1 mM EDTA, 0.1% SDS), followed by elution of the poly(A)$^+$ RNA with 3 vols of elution buffer (10 mM Tris-Cl, pH 7.6, 1 mM EDTA, 0.05% SDS) preheated to +65° C., by collecting 500 µl fractions. The $OD_{260}$ was read for each collected fraction, and the mRNA containing fractions were pooled and ethanol precipitated at −20° C. for 12 h. The poly(A)$^+$ RNA was collected by centrifugation, resuspended in DEPC-DIW and stored in 5–10 µg aliquots at −80° C.

Northern Blot Analysis

The poly(A)$^+$ RNAs (5 µg/sample) from various mycelia were electrophoresed in 1.2 agarose-2.2 M formaldehyde gels (Sambrook et al., 1989) and blotted to nylon membranes (Hybond-N, Amersham) with 10×SSC (Sambrook et al., 1989) as transfer buffer. Three random-primed (Feinberg & Vogelstein, 1983) $^{32}$P-labeled cDNA probes were used in individual hybridizations: 1) a 1.3 kb Not I-Spe I fragment for polygalacturonase I from *A. aculeatus,* 2) a 1.3 kb Not I-Spe I fragment encoding endoglucanase I from *A. aculeatus and* 3) a 1.2 kb Eag I fragment coding for galactanase I from *A. aculeatus*. Northern hybridizations were carried out in 5×SSC (Sambrook et al., 1989), 5×Denhardt's solution (Sambrook et al., 1989), 0.5% SDS (w/v) and 100 µg/ml denatured salmon sperm DNA with a probe concentration of ca. 2 ng/ml for 16 h at 65° C. followed by washes in 5×SSC at 65° C. (2×15 min), 2×SSC, 0.5% SDS (1×30 min), 0.2×SSC, 0.5% SDS (1×30 min), and 5×SSC (2×15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA Synthesis

First Strand Synthesis

Double-stranded cDNA was synthesized from 5 µg of *A. aculeatus* poly(A)$^+$ RNA by the RNase H method (Gubler & Hoffman 1983, Sambrook et al., 1989) using the hair-pin modification. The poly(A)$^+$RNA (5 µg in 5 µl of DEPC-treated water) was heated at 70° C. for 8 min., quenched on ice, and combined in a final volume of 50 µl with reverse transcriptase buffer (50 mM Tris-Cl, pH 8.3, 75 mM KCl, 3 mM MgCl2, 10 mM DTT, Bethesda Research Laboratories) containing 1 mM each dNTP (Pharmacia), 40 units of human placental ribonuclease inhibitor (RNasin, Promega), 10 µg of oligo(dT)$_{12-18}$ primer (Pharmacia) and 1000 units of SuperScript II RNase H- reverse transcriptase (Bethesda Research Laboratories). First-strand cDNA was synthesized by incubating the reaction mixture at 45° C. for 1 h.

Second Strand Synthesis

After synthesis 30 μl of 10 mM Tris-Cl, pH 7.5, 1 mM EDTA was added, and the mRNA:cDNA hybrids were ethanol precipitated for 12 h at −20° C. by addition of 40 μg glycogen carrier (Boehringer Mannheim) 0.2 vols 10 M $NH_4Ac$ and 2.5 vols 96% EtOH. The hybrids were recovered by centrifugation, washed in 70% EtOH, air dried and resuspended in 250 μl of second strand buffer (20 mM Tris-Cl, pH 7.4, 90 mM KCl, 4.6 mM MgCl2, 10 mM $(NH_4)_2SO_4$, 16 μM βNAD$^+$) containing 100 μM each dNTP, 44 units of *E. coli* DNA polymerase I (Amersham), 6.25 units of RNase H (Bethesda Research Laboratories) and 10.5 units of *E. coli* DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung Bean Nuclease Treatment

The double-stranded (ds) cDNA was ethanol precipitated at −20° C. for 12 h by addition of 2 vols of 96% EtOH, 0.1 vol 3 M NaAc, pH 5.2, recovered by centrifugation, washed in 70% EtOH, dried (SpeedVac), and resuspended in 30 μl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 μl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA Polymerase

The ds cDNA was blunt-ended with T4 DNA polymerase in 50 μl of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor Ligation and Size Selection

After the fill-in reaction the cDNA was ligated to non-palindromic BstX I adaptors (1 μg/μl, Invitrogen) in 30 μl of ligation buffer (50 mM Tris-Cl, pH 7.8, 10 mM MgCl2, 10 mM DTT, 1 mM ATP, 25 μg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of cDNA Libraries

The adapted, ds cDNA was recovered by centrifugation, washed in 70% EtOH and resuspended in 25 ml DIW. Prior to large-scale library ligation, four test ligations were carried out in 10 μl of ligation buffer (same as above) each containing 1 μl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector either pYES 2.0 vector Invitrogen or yHD17). The ligation reactions were performed by incubation at +16° C. for 12 h, heated at 70° C. for 5 min, and 1 μl of each ligation electroporated (200 Ω, 2.5 kV, 25 μF) to 40 μl competent *E. coli* 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h, 50 μl plated on LB+ampicillin plates (100 μg/ml) and grown at +37° C. for 12 h.

Using the optimal conditions a large-scale ligation was set up in 40 μl of ligation buffer containing 9 units of T4 ligase, and the reaction was incubated at +16° C. for 12 h. The ligation reaction was stopped by heating at 70° C. for 5 min, ethanol precipitated at −20° C. for 12 h, recovered by centrifugation and resuspended in 10 μl DIW. One μl aliquots were transformed into electrocompetent *E. coli* 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 μl of −80° C. bacterial stock propagated overnight.

Construction of Yeast Libraries

To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Ω, 1.5 kV, 25 μF) into 40 μl competent *S. cerevisiae* JG 169 cells (OD600=1.5 in 500 ml YPD, washed twice in cold DIW, once in cold 1 M sorbitol, resuspended in 0.5 ml 1 M sorbitol, Becker & Guarante, 1991). After addition of 1 ml 1M cold sorbitol, 80 μl aliquots were plated on SC+glucose−uracil to give 250–400 c.f.u./plate and incubated at 30° C. for 3–5 days.

Isolation of a cDNA Gene for Expression in Aspergillus

One or more of protease-producing colonies were inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9 M sorbitol, 0.1 M EDTA, pH 7.5. The pellet was transferred to an Eppendorf tube, and spun for 30 seconds at full speed. The cells were resuspended in 0.4 ml 0.9 M sorbitol, 0.1 M EDTA, 14 mM β-mercaptoethanol. 100 μl 2 mg/ml Zymolase was added, and the suspension was incubated at 37° C. for 30 minutes and spun for 30 seconds. The pellet (spheroplasts) was resuspended in 0.4 ml TE. 90 μl of (1.5 ml 0.5 M EDTA pH 8.0, 0.6 ml 2 M Tris-Cl pH 8.0, 0.6 ml 10% SDS) was added, and the suspension was incubated at 65° C. for 30 minutes. 80 μl 5 M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% ETOH, spun for 30 seconds and dried at room temperature. The pellet was resuspended in 50 μl TE and spun for 15 minutes. The supernatant was transferred to a fresh tube. 2.5 μl 10 mg/ml RNase was added, followed by incubation at 37° C. for 30 minutes and addition of 500 μl isopropanol with gentle mixing. The mixture was spun for 30 seconds, and the supernatant was removed. The pellet was rinsed with cold 95% EtOH and dried at room temperature. The DNA was dissolved in 50 μl water to a final concentration of approximately 100 μl/ml.

Transformation of *Aspergillus oryzae* or *Aspergillus niger* (General Procedure)

100 ml of YPD (Sherman et al., Methods in Yeast Genetics, Cold Spring Harbor Laboratory, 1981) is inoculated with spores of *A. oryzae* or *A. niger* and incubated with shaking at 37° C. for about 2 days. The mycelium is harvested by filtration through miracloth and washed with 200 ml of 0.6 M $MgSO_4$. The mycelium is suspended in 15 ml of 1.2 M $MgSO_4$. 10 mM $NaH_2PO_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6 M sorbitol, 100 mM Tris-HCl, pH=7.0. Centrifugation is performed for 15 minutes at 100 g and the protoplasts are collected from the top of the $MgSO_4$ cushion. 2 volumes of STC (1.2 M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an *A. nidulans* amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on the appropriate plates. Protoplasts are spread on minimal plates (Cove Biochem.Biophys.Acta 113 (1966) 51–56) containing 1.0 M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Immunological Cross-reactivity

Antibodies to be used in determining immunological cross-reactivity may be prepared by use of a purified protease. More specifically, antiserum against a protease of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Media

YPD: 10 g yeast extract, 20 g peptone, $H_2O$ to 810 ml. Autoclaved, 90 ml 20% glucose (sterile filtered) added.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC—H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC—H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of 40% glucose solution, 1.5 ml of a 1% L-leucine solution and 1.5 ml of a 1% histidine solution were added per 450 ml agar.

YNB-1broth: Composition as YNB-1 agar, but without the agar.

FG-4-Agar: 35 g/L agar, 30 g/L Sor bean meal, 15 g/L maltodextrin (Glucidex 6), 5 g/L Bacto pepton, pH 7. Autoclaved 40 min at 121° C.

FG-4 medium: 30 g/L Soy bean meal, 15 g/L maltodextrin (Glucidex 6), 5 g/L Bacto peptone. Autoclaved 40 min at 121° C.

MDU-2 medium: 45 g/L maltose, 1 g/L $MgSO_4$-7 $H_2O$, 1 g/L NaCl, 2 g/L $K_2SO_4$, 12 g/L $KH_2PO_4$, 0.1 ml/L Pluronic 61 L, 0.5 ml/L Trace metal solution. pH 5.0. Autoclaved 20 min at 121° C. 15 ml/L 50% sterile filtered urea is added after autoclaving.

Casein overlayer gel: 1% agarose, 0.5% casein in a buffer with a pH of 5.5. The gel was boiled and then cooled to 55° C. before the overlayer was poured onto agar plates.

Fed Batch Fermentation

The medium used for fed-batch fermentation of protease I or II by *A. oryzae* comprised maltodextrin as a carbon source, urea as a nitrogen source and yeast extract.

The fed batch fermentation was performed by innoculating a shake flask culture of the *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The fed batch cultivation was continued for 4 days, after which the enzymes could be recovered.

Characterization of Enzymes

Proteolytic Activity 1 hemoglobin protease unit (hpu) is defined as the amount of enzyme liberating 1 millimole of primary amino groups (determined by comparison with a serine standard) per minute under standard conditions as described below:

A 2% (w/v) solution of hemoglobin (bovine, supplied by Sigma) is prepared with the Universal Buffer described by Britton and Robinson, *J. Chem. Soc.,* 1931, p. 1451), adjusted to a pH of 5.5. 2 ml of the substrate solution are pre-incubated in a water bath for 10 min at 25° C. 1 ml of an enzyme solution containing b g/ml of the enzyme preparation, corresponding to about 0.2–0.3 hpu/ml of the Universal Buffer (pH 5.5) is added. After 30 min. of incubation at 25° C., the reaction is terminated by the addition of a quenching agent (5 ml of a solution containing 17.9 g of trichloroacetic acid, 29.9 g of sodium acetate and 19.8 g of acetic acid made up to 500 ml with deionized water). A blank is prepared in the same way as the test solution with the exception that the quenching agent is added prior to the enzyme solution. The reaction mixtures are kept for 20 min. in a water bath after which they are filtered through Whatman 42 paper filters.

Primary amino groups are determined by their colour development with o-phthaldialdehyde (OPA), as follows: 7.62 g of disodium tetraborate decahydrate and 2.0 g of sodium dodecylsulfate are dissolved in 150 ml of water. 160 mg of OPA dissolved in 4 ml of methanol were then added together with 400 µl of β-mercaptoethanol after which the solution is made up to 200 ml with water. To a 3 ml of the OPA reagent are added 400 µl of the filtrates obtained above, with mixing. The optical density (OD) at 340 nm is measured after about 5 min. The OPA test is also performed with a serine standard containing 10 mg of serine in 100 ml of Universal Buffer (pH 5.5). The buffer alone is used as a blank. The protease activity is calculated from the OD measurements by means of the following formula:

hpu/ml enzyme solution:

$$\frac{(OD_t - OD_b) \times C_{ser} \times Q}{(OD_{ser} - OD_B) \times MW_{ser} \times t_i} \text{ hpu/g of enzyme preparation} = \text{hpu/ml}: b$$

wherein $OD_t$, $OD_b$, $OD_{ser}$ and $OD_B$ is the optical density of the test solution, blank, serine standard and buffer, respectively, $c_{ser}$ is the concentration of serine (mg/ml) in the standard (in this case 0.1 mg/ml), and $MW_{ser}$ is the molecular weight of serine (105.09). Q is the dilution factor for the enzyme solution (in this case 8) and $t_i$ is the incubation time in minutes (in this case 30 minutes).

Inhibition

The following inhibitors were tested:

Pepstatin (aspartic acid inhibitor) (1 mM)

PMSF (serine protease inhibitor) (0.1%)

PEFABLOC (serine protease inhibitor) (0.1%)

EDTA (metallo protease inhibitor) (0.1M)

all available from Sigma except for PEFABLOC which is available from Pentapharm, Basel, Switzerland.

Residual activity was determined as HPU/l at pH 5.5.

pH activity profiles were determined as HPU/l at different pH values (4–8).

pH-stability was determined by letting an enzyme solution (0.3 HPU/l) stand for 30, 60 and 120 minutes, respectively, at 50° C. and different pH-values (4-5-6-7-8) and measure proteolytic activity before and after standing.

Temperature activity profiles were determined as HPU/l at different temperatures (15–70° C.).

Temperature stability was determined by letting an enzyme solution (0.3 HPU/l) stand for 30, 60 and 120 minutes at pH 5 and at different temperatures (25-40-50-60° C.), and measure proteolytic activity before and after standing.

SDS gel electrophoresis and isoelectric focusing was carried out on the Phast-System from Pharmacia using a Gradient 8–25 and the IEF 3–9, respectively, according to the manufacturers instructions.

Specificity

The specificity of proteases of the invention is determined as follows:

0.5 ml of 1 mg/ml human insulin or bovine glucagon in Universal Buffer, pH 5.5 (vide supra), and 75 µl of protease I and II, respectively, (0.6 hpu/l) in the same buffer were incubated for 120 min. at 37° C. The reaction was terminated by adding 50 µl 1N hydrochloric acid.

The insulin or glucagon molecule was cleaved into a number of peptide fragments. These were separated and isolated by reverse phase HPCL using a suitable C-18 column (Hibar LiChrosorb RP-18, 5 µm particles provided by Merck AG, Darmstadt, FRG). The fragments were eluted with the following solvents:

A. 0.2 M sodium sulfate and 0.1 M phosphoric acid, pH 2.5;

B. Acetonitrile/water, 50%;

on a linear gradient of from 90% A/10% B to 80% A/20% B for 0–5 min. and subsequently for 50 min. with 80% A/20% B. The isolated fragments were subjected to amino acid sequencing by automated Edman degradation, using an Applied Biosystems (Foster City, Calif., USA) Model 470A gas-phase sequencer, and the phenylthiohydantoin (PTH-) amino acids were analyzed by high performance liquid chromatography as described by L. Thim et al., "Secretion of human insulin by a transformed yeast cell", *FEBS Letters* 212(2), 1987, p.307, whereby the cleavage sites in the insulin or glucagon molecule were identified.

EXAMPLE 1

A library from *A. aculeatus* consisting of approx. $1.5 \times 10^6$ individual clones in 150 pools was constructed.

DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates. One set of plates was then incubated for 2–4 days at 30° C. and overlayered with a casein overlayer gel for detection of protease activity. After incubation overnight at 30° C., protease-positive colonies were identified as colonies surrounded by a white halo.

Cells from enzyme-positive colonies were spread for single colony isolation on agar, and an enzyme-producing single colony was selected for each of the protease-producing colonies identified.

The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical). The DNA sequences of two enzyme genes are shown in SEQ ID Nos. 1 and 2, respectively.

Subsequently, the cDNA encoding the protease was isolated for expression in Aspergillus as described above and transformed into E. coli using standard procedures. Two E. coli colonies were isolated from each of the transformations and analysed with the restriction enzymes HindIII and XbaI which excised the DNA insert. DNA from one of these clones was retransformed into yeast strain JG169.

The DNA sequences of several of the positive clones were determined. Two DNA sequences encoding a protease are shown in SEQ ID Nos. 1 and 2, respectively.

EXAMPLE 2

In order to express the genes in Aspergillus, cDNA is isolated from one or more representatives of each family using the above described procedure by digestion with HindIII/XbaI or other appropriate restriction enzymes, size fractionation on a gel and purification and subsequently ligated to pHD414, resulting in the plasmids pA1P1 and pA1P2. After amplification in E. coli, the plasmids are transformed into A. oryzae or A. niger according to the general procedure described above.

Test of A. oryzae Transformants

Each of the transformants was inoculated in the center of a Petri dish with FG-4 agar. After 5 days of incubation at 30° C. 4 mm diameter plugs were removed from the center of the colonies by means of a corkscrew. The plugs were embedded in a casein overlayer gel, containing 0.5% casein and 1% agarose in a buffer with a pH of 5.5, and incubated overnight at 40° C. The protease activity was identified as described above. Some of the transformants had halos which were significantly larger than the Aspergillus oryzae background. This demonstrates efficient expression of protease in Aspergillus oryzae. The 8 transformants with the highest protease activity were selected and inoculated and maintained on YPG-agar.

Each of the 8 selected transformants were inoculated from YPG-agar slants on 500 ml shake flask with FG-4 and MDU-2 media. After 3–5 days of fermentation with sufficient agitation to ensure good aeration, the culture broths were centrifuged for 10 minutes at 2000 g and the supernatants were analyzed.

A volume of 15 µl of each supernatant was applied to 4 mm diameter holes punched out in a casein overlayer gel (25 ml in a 13 cm diameter Petri dish). The protease activity was identified by the formation of a white halo on incubation.

Fed batch fermentation

Subsequently, protease I and II, respectively, were produced by fed batch fermentation of A. oryzae expressing the enzyme using the procedure described above.

EXAMPLE 3

Characterization of Protease I and II

The supernatant resulting from the fed batch fermentation above was used for the characterization performed as described in the Materials and Methods section above. Proteolytic activity was measured as HPU/l at pH 5.5 using the above described procedure.

Inhibition tests gave the following results:

|  | % Residual activity | | | |
| --- | --- | --- | --- | --- |
|  | EDTA | Pepstatin | PEFABLOC | PMSF |
| Protease I | 104 | 91 | 83 | 92 |
| Protease II | 97 | 9 | 90 | 108 |

The inhibition of Protease II by Pepstatin shows that it is an aspartic protease of the Pepsin type. Protease I is not inhibited by Pepstatin and is therefore not positively identified as an aspartic protease. Optimum activity at pH 5, on the other hand, shows that it is an acid protease. pH activity profiles are shown in FIG. 1. It is seen that both enzymes have optimum activity at pH 5, and that Protease I is active in a more narrow range than Protease II. Thus, protease I exhibits more than 60% activity in the range of pH 4–6, whereas Protease II exhibits more than 60% activity in the range of pH 4–7.

By SDS gel analysis the molecular weights of Protease I and II, respectively, were estimated to 23.000 and 37.000 kDa, respectively, From the IEF analysis of the pI of both enzymes are estimated to about 4.

FIG. 2 shows the temperature-activity profiles. They are rather similar for the two enzymes, but with slightly different optimum temperatures, 50° C. for Protease I and 45° C. for Protease II.

FIGS. 3 and 4 show the pH-stability. For each pH, the zero-time activities have been set to 100%, and the absolute values obtained are therefore different. Both proteases are stable at pH 4 and 5. At pH 6, Protease I is unstable, while Protease II has a certain stability (40% residual activity after 30 min). Both enzymes are unstable at pH 7.

FIGS. 5 and 6 show the temperature-stability. For each temperature, the zero-time activities have been set to 100%, and the absolute values obtained are different. Both proteases are stable up to 50° C., but unstable at 60° C.

Based on the results obtained on hydrolysis of insulin and glucagon by Protease I and Protease II it was found that Protease II does not react with insulin, whereas both proteases hydrolyse glucagon. It can be concluded, that Protease I is a rather unspecific protease, while Protease II is more specific. It was found that protease II is capable of cleaving the Lys-Tyr and the Phe-Val bonds found in bovine glucagon (the sequence of which is shown in Bromer, Sinn, and Behrens, J. Amer. Chem. Soc., Vol. 79, p. 2807, 1958).

EXAMPLE 4

Use of a Protease of the Invention for Viscosity Reduction

Soy flour (prepared from defatted and peeled soy beans) were pelletized at 95° C. and grinded afterwards. The soy flour is suspended in deionized water to 15% dry substance. 5 mg protease I enzyme protein per g of dry substance and 5 mg protease II enzyme protein per g of dry substance, respectively, was added to the soy slurry. The slurry was incubated at 40° C. and pH 5–6. The viscosity in the slurry was measured after 1, 2 and 24 hours of incubation on a Brookfiled LV DV III viscometer using a small sample adaptor with spindle #31 at 250 rpm. The residual viscosities were as follows:

|         | Prot. I | Prot. II |
|---------|---------|----------|
| 1 hour  | 73%     | 47%      |
| 2 hours | 59%     | 38%      |

EXAMPLE 5

Use of a Protease of the Invention for Cleaning of Contact Lenses

In the field of contact lens cleaning it is essential to regularly have both an efficient disinfection and cleaning of the contact lens. One of the most effective ways of disinfecting contact lenses is to immerse them into a solution containing 3% $H_2O_2$ at pH 3.5 for at least 20 minutes. The $H_2O_2$ is neutralized with e.g. catalase or a platinum disc before inserting the lens into the eye. Unfortunately no commercially interesting protease till date has been shown to have good effect under these harsh conditions, so a cumbersome second step with addition of a protease after $H_2O_2$-neutralization is needed to remove the protein deposits on the contact lens. Porcine pepsin is superior to the presently used serin protease. (*Subtilisin carlsberg*) but is troublesome because of the viruses often associated with mammal products.

Protease I and II, respectively, of the invention have been tested with respect to the ability to remove denaturated protein from a contact lens. They have been compared to the presently used serin protease and also to porcine pepsin, although the latter is interesting from a technical perspective rather than a commercial perspective.

The experimental protocol was as follows:
Materials: Hen Lysozyme, L-6878 from Sigma "Rythmic" contact lens' from Essilor (Type II lens, highwater, nonionic) Protease I produced as described above Protease II produced as described above Porcine pepsin, P-6887 from Sigma *Subtilisin carlsberg*, Clear-Lens Pro® (Novo Nordisk A/S).

Standard buffer: 0.05 M $Na_2HPO_4$, 0.9% NaCl pH 7.5
Reagent buffer: 0.05 M $Na_2HPO_4$, 0.9% NaCl, 3% $H_2O_2$, pH 3.5
Scintillation liquid, Optiphase "HiSafe III"

Hen lysozyme from Sigma was labelled with $^{14}C$ through reductive methylation and purified.

A solution was made containing 0.05 M $Na_2HPO_4$, 0.9% NaCl and 0.2 mg/ml lysozyme pH 7.5. An amount of $^{14}C$-labelled lysozyme was added so the CPM (Counts Per Minute) is approximately 200.000. 1.0 ml of the solution was transferred to a scintillation glass. The contact lens was added and the glass placed in a water-bath at 85° C. for 30 minutes.

The contact lens was then rinsed in 3×3 ml reagent buffer. It was quartered with a scalpel. Each quarter was transferred to a new scintillation glass containing 3 ml of the reagent buffer.

Different amounts of the protease to be tested were added so the final concentrations were 0.1, 0.5, 2.5, 5, 12.5, 50 and 200 µg enzyme protein/ml reagent buffer.

The reaction took place over four hours at 25° C. The quarter lenses were rinsed in 2×3 ml standard buffer. 12 ml scintillation liquid was added and CPM was measured in a Packard 2500 TR liquid scintillation counter.

Four lenses were needed to evaluate each protease: Double determinations were made over two days, and a blind reference was needed for each lens.

The relative amount of lysozyme removed from the lens during the combined disinfection/cleaning was calculated from the mass balance of each quarter lens. FIG. 7 gives a graphic presentation of the performance of the different proteases.

Both proteases are high suitably for contact lens cleaning purposes. Protease I was found to be very superior to the other proteases. Protease II is very close to porcine pepsin in performance whereas the presently used serin protease shows poor performance. A further advantage of the acidic proteases of the invention is the low activity at the neutral pH found in tear fluid. This lowers the risk of irritation if the lenses are not rinsed properly after disinfection/cleaning.

EXAMPLE 6

Use of a Protease of the Invention for Baking

Procedure:
To 10 grams of cake flour 5.9 g of water are added. The water contains different concentrations of Protease I, Protease II and Neutrase® (available from Novo Nordisk A/S). The dough is mixed on a Glutamic 2200 mixer for one minut. It is then placed in a plastic bag and is incubated for 25 min. at 32° C.

Thereafter the dough is washed with 2% NaCl (aqeuous solution) using the Glutamic mixer in order to remove starch and leave gluten in the dough.

The gluten lump is then rolled by hand untill homogeneity and is pressed into the shape of a cylinder which is about 0.5 cm high and 2.5 cm in diameter and has a hole in the center. The gluten lump is pressed into shape for 30 min at 25° C. Subsequently, the gluten cylinder is hung on a hook and a 2 g weight is placed in the hole. Everything is placed under water at 25° C.

The stretching of the gluten cylinder is thereafter measured every 15 min untill it breaks.

Enzymes are dosed on an Anson Unit basis (AU), initially trying with 7.5 mAU/kg flour, which is the optimal dose for Neutrase®. (In the Anson-Hemoglobin method for the determination of porteolytic activity denatured hemoglobin is digested at a temperature of 25° C., pH 7.5 and a rection time of 10 min. The undigested hemoglobin is precipitated with trichloroacetic acid (TCA) and the amount of TCA soluble product is determined with phenol reagent, which gives a blue colour with tyrosine and tryptophan. 1 AU is the amount of enzyme which digests hemoglobin at an initial rate such that there is liberated per minute an amount of TCA soluble product which gives the same colour with phenol reagent as one milliequivalent of tyrosine).

FIG. 8 shows the stretching curves of gluten without enzyme and with Neutrase®, Protease I and Protease II. The curves are means of 6–7 determinations with the same dose of enzyme. As can be seen, the addition of all 3 proteases led to a faster stretching of the gluten.

Protease I in a dose of 7.5 mAU/kg flour does not weaken the gluten as much as the same dose of Neutrase®. The gluten cylinder gets longer before it breaks, and the rate of elongation is lower.

Addition of 2.3 mAU/kg flour of protease II, which was the largest amount possible in this system, almost weakens the gluten as much as 7.5 mAU/kg of Neutrase®. The gluten breaks a little later, and the shape of the curves are not identical. This shows that protease II is approximately 3 times as efficient on an AU basis as Neutrase® for gluten weakening.

In conclusion the proteases of the invention constitutes a desirable alternative to chemicals conventionally used for gluten weakening, a widely used example of which is SMS (sodium metabisulphite).

EXAMPLE 7

Use of a Protease of the Invention for Animal Feed

Ground defatted feed quality soy was mixed with deionised water under the conditions described below. The hydrolysis was carried out in two steps in order to simulate the pH conditions in the stomach and the small intestine. The performance of Protease II of the invention was compared with that of Bio-Feed Pro, which by Brenes et al., 1993, has been demonstrated to result in improved weight gain and feed efficiency when used in broiler diets.

| Hydrolysis conditions: | | |
|---|---|---|
| Hydrolysis mixture | 70 g ground defatted soy | |
|  | 330 g deionised water | |
| Temperature | 40° C. | |
| pH | 1st step | 4.0 |
|  | 2nd step | 6.5 |
| Time | 1st step | 180 minutes |
|  | 2nd step | 180 minutes |
| Enzymes | 1st step | I) Pepsin 1.92 g |
|  |  | (Merck art. 7190) |
|  |  | II) I + Bio-Feed Pro 3.0 L |
|  |  | 5.5 AU/kg soya |
|  |  | III) I + protease II |
|  |  | 0.19 AU/kg soya |
|  | 2nd step | I) Pancreatin 6 g |
|  |  | (Sigma P 1750) |
|  |  | II) I + Bio-Feed Pro 3.0 L |
|  |  | 5.5 AU/kg soya |
|  |  | III) I + Protease II |
|  |  | 0.19 AU/kg soya |

Bio-Feed Pro® is available from Novo Nordisk A/S. Protease II was obtained as described above.

The enzymes were added at start 0 minutes. During the hydrolysis °Brix and osmolality were measured to follow the reaction course. According to Adler-Nissen (1986) the osmolality values can be used for calculation of the Degree of Hydrolysis (DH) by the following equation:

$$DH = \frac{\Delta C}{S\% \times f_{osm}} \times \frac{1}{\omega} \times \frac{1}{h_{tot}} \times 100\%$$

Where $\Delta$ is the increase in osmolality mOSM, S% is protein concentration, $\omega$ is the calibration factor for the osmometer, $h_{tot}$ is the total number of peptide bonds in the protein substrate (megv/g protein), and $f_{osm}$ is the factor for converting % to g/kg H$_2$O.

$$f_{osm} = \frac{1000}{100 - DM\%} =$$

Further the average Molecular Weight was analysed of the sulpho salicylic acid soluble phase of the N-components of the hydrolysis mixture after 90 minutes (1step) and 0, 15 and 180 minutes (2nd step). The Molecular Weight analyses were performed by the following method:

1. Principle

The sample is diluted, filtrated and injected into a liquid chromatographic system, operating in the Gel Permeation Chromatography (GPC) mode. This separation technique utilizes a liquid flow through a column filled with porous particles having pores with a well-defined pore diameter. When a solution of peptides having different molecular size passes through the column, the small peptides will be able to flow into the pores while the larger peptides will be excluded from the pores. Thus, the peptides in a solution will be separated according to molecular size (and weight) as the large peptides will be eluted faster from the column than the small peptides. A detector at the column outlet continuously measures the effluent. The chromatographic system is calibrated with peptides with known molecular weight.

2. Chromatographic equipment 2.1 HPLC system consisting of

High Pressure pump, WATERS M 510, flow rate 0.7 ml/min.

Injector, Waters WISP M 710

Detector, Waters M 440, with wavelength extension to 214 nm.

2.2 GPC column, 3×TSK G 2000 SWXL, 7.8 mm×300 mm, connected in series and operated at ambient temperature.

2.3 Integration/data processing, Waters 820 MAXIMA SIM chromatography data system with 810/820 GPC option.

3. Reagents 3.1 Phosphate buffer, NaH$_2$PO$_4$ 2H$_2$O 3.2 Ammoniumchloride, NH$_4$CL 3.3 Trifluoroacetic acid (TFA), CF$_3$COOH 3.4 Acetonitrile, CH$_3$CN 3.5 Mobile phase:

0.05 M Phosphate buffer/0.5 M Ammoniumchloride solution containing 0.1% TFA and 25% Acetonitrile 4. Description 4.1 Calibration The chromatographic system is calibrated by means of injections of numerous peptide standards with known molecular weight. The molecular weight of each standard is plotted semilogarithmic versus the observed volume of mobile phase needed to elute the peptide from the column. By a least squares calculation the best fitting 3rd order polynomium is calculated. This curve represents the calibration curve.

4.2 Analysis

The sample is diluted/dissolved in mobile phase to approx. 5 mg/ml. The solution is filtered through a 22 $\mu$m filter and 20 $\mu$l is used for injection into the chromatograph. The detector response versus elution volume is recorded. The recorded curve—the chromatogram—shows the actual molecular weight distribution of the sample. To allow for calculations as to accumulated weight distribution and average molecular weight calculations, the chromatogram is divided into small time (and elution volume) segments—each segment being characterized by the elution volume and the area of the chromatogram over the time interval.

5. Calculation

Results are given in terms of weight and number average molecular weights.

$$\overline{M}_w = \frac{\Sigma_i(A_i * M_{w,i})}{\Sigma_i A_i}, \quad \overline{M}_n = \frac{\Sigma_i A_i}{\Sigma_i(A_i / M_{w,i})},$$

where $\overline{M}_w$: Weight average molecular weight $\overline{M}_n$: Number average molecular weight $A_i$: Area of chromatogram for each segment, measured as the accumulated detector response over each time interval.

$M_{w,i}$: The corresponding molecular weight for each segment. The value is calculated by means of the calibration curve using the average elution volume over the time interval.

RESULTS

The values for °Brix, mOSM and %DH are given in the table below:

| HYDROLYSIS OF FEED SOY WITH PEPSIN, BIO-FEED PRO, PROTEASE II AND PANCREATIN ||||||||||
|---|---|---|---|---|---|---|---|---|---|
| PARAMETER: ° BRIX ||||||||||
| STEP I, MIN. ||||||||||
| ENZYME | 0 | 5 | 10 | 15 | 30 | 45 | 60 | 90 | 120 | 180 |
| PEPSIN | 5.09 | 6.135 | 6.505 | 6.625 | 6.9275 | 7.345 | 7.745 | 8.175 | 8.695 | 9.195 |
| BIO-FEED PRO | 5.09 | 6.125 | 6.325 | 6.545 | 7.245 | 7.465 | 7.565 | 8.185 | 8.545 | 9.105 |
| PROTEASE II | 5.09 | 6.505 | 6.845 | 7.105 | 7.825 | 8.405 | 8.605 | 9.305 | 9.705 | 10.205 |
| STEP II, MIN. ||||||||||
| ENZYME | 180 | 185 | 190 | 195 | 210 | 225 | 240 | 270 | 300 | 360 |
| PEPSIN | 12.965 | 15.135 | 15.4025 | 15.637 | 16.135 | 16.415 | 16.705 | 17.075 | 17.437 | 18.075 |
| BIO-FEED PRO | 12.965 | 15.165 | 15.165 | 15.125 | 16.105 | 16.4 | 16.525 | 16.885 | 17.285 | 17.805 |
| PROTEASE II | 13.605 | 15.605 | 15.925 | 16.025 | 16.365 | 16.685 | 16.885 | 17.105 | 17.505 | 18.145 |
| PARAMETER: mOSM ||||||||||
| STEP I, MIN. ||||||||||
| ENZYME | 0 | 5 | 10 | 15 | 30 | 45 | 60 | 90 | 120 | 180 |
| PEPSIN | 347 | 362 | 362 | 360.5 | 363.5 | 366 | 368 | 370.5 | 373 | 381.5 |
| BIO-FEED PRO | 347 | 365 | 364 | 366 | 367 | 371 | 373 | 379 | 380 | 385 |
| PROTEASE II | 347 | 371 | 382 | 391 | 411 | 421 | 427 | 439 | 447 | 463 |
| STEP II, MIN. ||||||||||
| ENZYME | 180 | 185 | 190 | 195 | 210 | 225 | 240 | 270 | 300 | 360 |
| PEPSIN | 468 | 996 | 1009 | 1015.5 | 1037.5 | 1054.5 | 1068.5 | 1087.5 | 1111 | 1148 |
| BIO-FEED PRO | 468 | 1013 | 1017 | 1033 | 1048 | 1058 | 1069 | 1094 | 1113 | 1145 |
| PROTEASE II | 548 | 1118 | 1127 | 1135 | 1152 | 1161 | 1176 | 1201 | 1227 | 1284 |
| PARAMETER: mOSM INCREASE ||||||||||
| STEP I, MIN. ||||||||||
| ENZYME | 0 | 5 | 10 | 15 | 30 | 45 | 60 | 90 | 120 | 180 |
| PEPSIN | 0 | 15 | 15 | 13.5 | 16.5 | 19 | 21 | 23.5 | 26 | 34.5 |
| BIO-FEED PRO | 0 | 18 | 17 | 19 | 20 | 24 | 26 | 32 | 33 | 38 |
| PROTEASE II | 0 | 24 | 35 | 44 | 64 | 74 | 80 | 92 | 100 | 116 |
| STEP II, MIN. ||||||||||
| ENZYME | 180 | 185 | 190 | 195 | 210 | 225 | 240 | 270 | 300 | 360 |
| PEPSIN | 0 | 528 | 541 | 547.5 | 569.5 | 586.5 | 600.5 | 619.5 | 643 | 680 |
| BIOFEED PRO | 0 | 545 | 549 | 565 | 578 | 590 | 601 | 626 | 645 | 677 |
| PROTEASE II | 0 | 570 | 579 | 587 | 604 | 613 | 628 | 653 | 679 | 736 |
| PARAMETER: % DH ||||||||||
| STEP I, MIN. ||||||||||
| ENZYME | 0 | 5 | 10 | 15 | 30 | 45 | 60 | 90 | 120 | 180 |
| PEPSIN | 0 | 2.86 | 2.86 | 2.57 | 3.14 | 3.62 | 4.00 | 4.47 | 4.95 | 6.57 |
| BIO-FEED PRO | 0 | 3.43 | 3.24 | 3.62 | 3.81 | 4.57 | 4.95 | 6.09 | 6.28 | 7.24 |
| PROTEASE II | 0 | 4.57 | 6.66 | 8.38 | 12.19 | 14.09 | 15.23 | 17.52 | 19.04 | 22.09 |

The results of the molecular weight analysis is given below:

|  | Step I | Step II ||
|---|---|---|---|
|  | 90 min | 0 min | 15 min | 180 min |
| Pepsin | 960 | 1070 | 680 | 520 |
| Bio-Feed Pro | 880 | 1020 | 690 | 510 |
| Protease II | 650 | 630 | 530 | 480 |

The apparent Molecular Weight is increased when pH is adjusted to 6.5 as undigested soy protein is more soluble at pH 6.5 than at pH 4.0.

It is seen that protease II releases more protein and peptides and degrade the proteins more than Bio-Feed Pro, it therefore concluded that protease II is superior to Bio-Feed Pro.

Since protease II of the invention has optimum activity in acid pH range, this enzyme will therefore perform already in the stomach of the animal, thus an overall improvement on feed efficiency should be achieved compared to Bio-Feed Pro when applied in feed for young animals. The above results supports this conclusion.

REFERENCES

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989, Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74: 5463–5467.

Brenes, A. et al., Poultry Science, 72, 2281–2293, 1993.

Adler-Nissen, J. Enzymic Hydrolysis of Food Proteins, Elsevier Applied Science Publishers London and New York, 1986.

Takahashi K. et al., 1991, The Primary Structure of *Aspergillus niger* Acid Proteinase A*, The Journal of Biol. Chemistry, Vol. 266, No. 29, pp. 19480–19483.

Choi, G. H. et al., Molecular analysis and overexpression of the gnee encoding endothiapepsin, an aspartic protease from *Cryphonectria parasitica*, 1993, Gene 125:135–131.

Gomi, K. et al., 1993, Cloning and Nucleotide Sequence of the Acid Protease-encoding Gene (pepA) from *Aspergillus oryzae*, Biosci. Biotech. Biochem., 57(7):1095–1100.

Inoue, H. et al., 1991, The Gene and Deduced Protein Sequences of the Zymogen of *Aspergillus niger* Acid Proteinase A*, The Journal of Biological Chemistry, Vol. 266, No. 29, pp. 19484–19489.

Berka, R. M. et al., 1993, Isolation and characterization of the *Aspergillus oryzae* gene encoding aspergillopepsin O, Gene, 125:195–198.

Berka, R. M. et al., 1990, Molecular cloning and deletion of the gene encoding aspergillopepsin A from *Aspergillus awamori*, Gene 86:153–162.

Berka, R. M. et al., 1990, Corrigendum, Molecular cloning and deletion of the gene encoding aspergillopepsin A from *Aspergillus awamori*, Gene 96:313.

What is claimed is:

1. A method for cleaning a contact lens comprising treating said contact lens with an effective amount of an isolated and purified enzyme exhibiting protease activity at a pH of 4–7 which exhibits protease activity in 5% hydrogen peroxide and which is encoded by a DNA sequence which hybridizes to a DNA sequence depicted in SEQ ID NO. 1 or 2 under the following conditions: hybridizing in 5×SSC, 5×Denhardt's solution, 0.5% SDS and 100 ug/ml salmon sperm DNA for 16 hrs. at about 65° C., followed by washes in 5×SSC, 2×SSC, 0.5% SDS, 0.2×SSC, 0.5% SDS and 5×SSC at 65° C.

2. The method according to claim 1, in which said enzyme is obtainable from a filamentous fungi.

3. The method according to claim 1, in which said enzyme is obtainable from a strain of Aspergillus, Rhizopus, Trichoderma, Penicillium, Fusarium, Schytalidium or Humicola.

4. The method according to claim 1, which is obtainable from a strain of *Aspergillus aculeatus*.

* * * * *

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 1124 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Aspergillus aculeatus (xi) SEQUENCE DESCRIPTION: SEQ ID NO:1:

```
AATTAAGCAT CCTCCATCTT CAAAGCTCAA TCTCGCTAAC TCCCGCTCTT CTCTCGATCT      60

CATCATCCCA ATAACTCGGA CACAATGAAG ACCTCTGCTC TCTTGACCGC TGGCCTGTTG     120

GCCACCGCTG CTATTGCTGC TCCTCTCACC GAGAAGCGCG CAGCTGCTCG CGCTGCCAAG     180

CGTGGCACCA GCCGCAAGAG CAACCCCCCT CTCAAGCCCG GCACCAGCGA GGCCATCAAC     240

CTGACCGGCT CCAAGAACAC CGAGTACTCG TCCAACTGGG CCGGCGCCGT GCTCATCGGC     300

ACCGGCTACA CTGCCGTCAC CGCCGAGTTC ACCATTCCCA CCCCCTCTCT CCCCTCCGGT     360

GCCTCCAGCC GCGAGCAGTA CTGTGCCTCC GCCTGGGTCG GTATCGACGG TGACACCTGC     420

GACACCGCCA TCCTGCAGAC CGGTCTCGAC TTCTGTATCG AGGGCAGCAC CGTTAGCTAC     480

GACGCCTGGT ACGAGTGGTA CCCCGACTAT GCCTACGACT TCAGCGGCAT CAGCTTCTCC     540

GCCGGCGACG TTGTCAAGGT CACCGTCGAC GCCACCAGCA AGACCGCCGG TACCGCCACC     600

GTCGAGAACG TCACCAAGGG CACCACCGTC ACCCACACCT TCAGCGGTGG TGTTGATGGT     660

GATCTCTGCG AGTACAACGC CGAGTGGATC GTCGAGGACT TCGAGGAGAA CTCCTCCCTC     720
```

```
GTCCCCTTCG CCGACTTCGG CACCGTCACC TTCTCCAGCG CCTACGCCAC CAAGAGCGGC    780

TCCACCGTTG GTCCCTCCGG CGCCACCATC ATCGACATCG AGCAGAACAA CAAGGTTCTC    840

ACCTCCGTCT CGACCTCCAG CAGCTCCGTC ACCGTCGAGT ATGTTTGAAG GGGACTCCTG    900

GGGATGTGAA GCGAGAATGC GGCTTGGGTG GTTGGAGGTC CTTTGGGACG TCGAACGCCT    960

AGGATTCAAC GGGATGAGAT CATTGGAAAT GAAGACGAGA ATGAGCGAAT ACTGTCACTG   1020

ATTGAGATTG TGCTTTGTTG ATTGTGTTAG GGGCTTGCCT CTGAAAATTG AGCTTAGTGT   1080

TGCTGCAATA TGATTGCTGT GGTTGAGAAA AAAAAAAAAA AAAA                   1124
```

(2) INFORMATION FOR SEQ ID NO:2:

(i) SEQUENCE CHARACTERISTICS:
        (A) LENGTH: 1425 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:2:

```
CTGCTTCTCC TTCTCTTCCT CCTCGTGATA TCTGCTTGAA CATCTCCTCA TCATGGTCGT     60

CCTCAACAAG GCTGCAGCCC TTCTTCTGGG TCTGACCACC GCCGCCACTG CGGCTCCCCT    120

GGCCGAGAAG CAGGCTTCTG TCCCGGTCAA GAACTTCTCC GTCAAGCAGG TCGAGAAGGA    180

GGGCAGCAAG GGACGTACCG TTAACCTGCC GGGTCTGTAT GCGAATGCGC TGGCCAAGTA    240

TGGCGCCCAG GTGCCGGCCA GCGTCAAGGC CGCCGCCGTC AGTGGCAGCG TCGTGACCAC    300

CCCGCAGGCC AACGACGTCT CCTACCTGAC CCCCGTCACC GTGGGCAGCT CGACCTTGAA    360

CCTGGACTTC GACACCGGAT CCGCCGATCT CTGGGTCTTC TCCTCGGAGC TGGCCGCCTC    420

CTCGCGCACC GGCCACAGCA TCTACACCCC CGGCAGCACC GCCCAGAAGC TGTCCGGCTA    480

CAGCTGGAGC ATCTCCTACG CGACGGCAG CTCCGCCAGC GGCGACGTCT ACAAGGACAA    540

GGTCACCGTC GGCACGGTGA CGGCCAGCAG CCAGGCCGTC GAGGCCGCCA GCCGCATCAG    600

CTCCGAGTTC GTCCAGGACA CCGACACCGA CGGTCTGTTG GGTCTGGCCT TCAGCTCGAT    660

CAACACGGTC TCCCCCCGGG CCCAGACCAC CTTCTTCGAC ACCGTCAAGT CCAGCCTGGA    720

CAGCCCCCTC TTCGCCGTCG ACCTGAAGTA CCACGCCGCC GGTACCTACG ATTTCGGGTT    780

CATCGACTCC TCCAAGTACA CCGGCTCCCT GACCTACGCC AACGTCGACG ACTCCCAGGG    840

CTTCTGGCAA TTCACCGCCA GCGGCTACAG CGTGGGCTCG GCCTCCCACT CCTCCTCTTT    900

CTCCGCCATT GATGACACCG GCACCACCCT CATCCTCCTC GACGACTCCA TCGTCTCCAC    960

CTACTACAAG AGCGTCAGCG GCGCCTCCTA CAGCTACAAC TACGGCGGCT ACGTCTTCTC   1020

CTGCTCCGCC AGCCTGTCCA ACTTCAGCGT CAAGATCGGC TCCTACACCG CCGTCGTCCC   1080

CGGCAAGTAC ATCAACTACG CCCCCATCTC CACCGGCAGC TCCACCTGCT ACGGCGGCAT   1140

CCAGTCCAAC GAGGGCCTCG GTCTGTCCAT CCTGGGTGAT GTCTTCCTCA AGAGCCAGCA   1200

CGTGGTCTTT GACTCGCAGG GTCCGAGAAT CGGGTTCGCC GCGCAGGCCT AGATCGTTTG   1260

ATTGGGGTTG TGGATGTGGG TGATGCTTGG TGGTGGTCTG AGTCGTGGTC TATGTGGGCG   1320

TGAATATAGT ACTGTATATA GTACTGTACA TAGGGGGGTG GTGAACATAT GGTCTGGTCG   1380
```

ATGAATATAT GTCTTTGATG TTATGCTTCT GTGGAAAAAA AAAAA    1425

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:3:

AATTAAGCAT CCTCCATCTT    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CAAAGCTCAA TCTCGCTAAC    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TCCCGCTCTT CTCTCGATCT    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:6:

CATCATCCCA ATAACTCGGA    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CAAAATGAAG ACCTCTGCTC                                                      20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:8:

TCTTGACCGC TGGCCTGTTG                                                      20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:9:

GCACCGCTGC TATTGCTGCT                                                      20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:10:

CCTCTCACCG CGAAGCGCGC                                                      20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:11:

ACGTGCTCGC GCTGCCAAGC                                       20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:12:

TGGCACCAGC CGCAAGAGCA                                       20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:13:

AGGGGGGTCT CAAGCCCGGC                                       20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO

```
        (iv) ANTI-SENSE: NO (vi) ORIGINAL SOURCE:
             (A) ORGANISM: Aspergillus aculeatus (xi) SEQUENCE DESCRIPTION: SEQ ID NO:14:

ACCCAGCGAG GCCATAACCT                                                    20

(2) INFORMATION FOR SEQ ID NO:15:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Aspergillus aculeatus (xi) SEQUENCE DESCRIPTION: SEQ ID NO:15:

GACCGGCTCC AAGAACACCG                                                    20

(2) INFORMATION FOR SEQ ID NO:16:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Aspergillus aculeatus (xi) SEQUENCE DESCRIPTION: SEQ ID NO:16:

GAGGTACTCG TCCAACTGGG                                                    20

(2) INFORMATION FOR SEQ ID NO:17:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Aspergillus aculeatus (xi) SEQUENCE DESCRIPTION: SEQ ID NO:17:

CCGGCGCCGT GCCAT                                                         15

(2) INFORMATION FOR SEQ ID NO:18:

(i) SEQUENCE CHARACTERISTICS:
```

(A) LENGTH: 295 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:18:

AATTAAGCAT CCTCCATCTT CAAAGCTCAA TCTCGCTAAC TCCCGCTCTT CTCTCGATCT    60

CATCATCCCA ATAACTCGGA CAAAATGAAG ACCTCTGCTC TCTTGACCGC TGGCCTGTTG   120

GCACCGCTGC TATTGCTGCT CCTCTCACCG CGAAGCGCGC ACGTGCTCGC GCTGCCAAGC   180

TGGCACCAGC CGCAAGAGCA AGGGGGGTCT CAAGCCCGGC ACCCAGCGAG GCCATAACCT   240

GACCGGCTCC AAGAACACCG GAGGTACTCG TCCAACTGGG CCGGCGCCGT GCCAT        295

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:19:

CTGCTTCTCC TTCTCTTCCT                                                20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:20:

CCTCGTGATA TCTGCTTGAA                                                20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Aspergillus aculeatus (xi) SEQUENCE DESCRIPTION: SEQ ID NO:21:

CATCTCCTCA TCATGGTCGT                                                          20

(2) INFORMATION FOR SEQ ID NO:22:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Aspergillus aculeatus (xi) SEQUENCE DESCRIPTION: SEQ ID NO:22:

CCTCAACAAG GTGCAGCCTT                                                          20

(2) INFORMATION FOR SEQ ID NO:23:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:23:

CTTCTGGGTC TGACCACCGC                                                          20

(2) INFORMATION FOR SEQ ID NO:24:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Aspergillus aculeatus (xi) SEQUENCE DESCRIPTION: SEQ ID NO:24:

CGCCACTGGT CCCCTGGCCG                                                          20

(2) INFORMATION FOR SEQ ID NO:25:

(i) SEQUENCE CHARACTERISTICS:
         (A) LENGTH: 20 base pairs
         (B) TYPE: nucleic acid
         (C) STRANDEDNESS: single (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Aspergillus aculeatus (xi) SEQUENCE DESCRIPTION: SEQ ID NO:25:

AGCCGCAGGC TTCTGTCCGG                                                    20

(2) INFORMATION FOR SEQ ID NO:26:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Aspergillus aculeatus (xi) SEQUENCE DESCRIPTION: SEQ ID NO:26:

TCAAGAACTT CTCCGTCAAG                                                    20

(2) INFORMATION FOR SEQ ID NO:27:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Aspergillus aculeatus (xi) SEQUENCE DESCRIPTION: SEQ ID NO:27:

CAGGTCGAGA AGGCGGGCAG                                                    20

(2) INFORMATION FOR SEQ ID NO:28:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Aspergillus aculeatus (xi) SEQUENCE DESCRIPTION: SEQ ID NO:28:

CAAGGGACGT ACCGTTAACC                                                    20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:29:

TGCCGGGTCT GTATGCGAAT                                                    20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:30:

GCGCTGGCCA AGTATGGCGC                                                    20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Aspergillus aculeatus (xi) SEQUENCE DESCRIPTION: SEQ ID NO:31:

CCAGGTGCGG CCAGCGTCAA                                                    20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA

```
        (iii) HYPOTHETICAL: NO (iv) ANTI-SENSE: NO (vi) ORIGINAL SOURCE:
              (A) ORGANISM: Aspergillus aculeatus (xi) SEQUENCE DESCRIPTION: SEQ ID NO:32:

GGCCGCCGCC GTCAGTGGCA                                                   20

(2) INFORMATION FOR SEQ ID NO:33:

(i) SEQUENCE CHARACTERISTICS:
              (A) LENGTH: 29 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vi) ORIGINAL SOURCE:
              (A) ORGANISM: Aspergillus aculeatus (xi) SEQUENCE DESCRIPTION: SEQ ID NO:33:

GCGTCGTGAC CACCCGCAGG CCAACGACG                                         29

(2) INFORMATION FOR SEQ ID NO:34:

(i) SEQUENCE CHARACTERISTICS:
              (A) LENGTH: 309 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vi) ORIGINAL SOURCE:
              (A) ORGANISM: Aspergillus aculeatus (xi) SEQUENCE DESCRIPTION: SEQ ID NO:34:

CTGCTTCTCC TTCTCTTCCT CCTCGTGATA TCTGCTTGAA CATCTCCTCA TCATGGTCGT        60

CCTCAACAAG GTGCAGCCTT CTTCTGGGTC TGACCACCGC CGCCACTGGT CCCCTGGCCG       120

AGCCGCAGGC TTCTGTCCGG TCAAGAACTT CTCCGTCAAG CAGGTCGAGA AGGCGGGCAG       180

CAAGGGACGT ACCGTTAACC TGCCGGGTCT GTATGCGAAT GCGCTGGCCA AGTATGGCGC       240

CCAGGTGCGG CCAGCGTCAA GGCCGCCGCC GTCAGTGGCA GCGTCGTGAC CACCCGCAGG       300

CCAACGACG                                                              309
```